(12) United States Patent
Kanehira et al.

(10) Patent No.: US 6,978,226 B2
(45) Date of Patent: Dec. 20, 2005

(54) DETERIORATION DIAGNOSTIC METHOD AND EQUIPMENT THEREOF

(75) Inventors: Katsumi Kanehira, Tokyo (JP); Yoko Todo, Tokyo (JP); Keiichi Sasaki, Tokyo (JP); Akira Sawada, Tokyo (JP); Kenji Adachi, Tokyo (JP); Kazushige Kimura, Tokyo (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 145 days.

(21) Appl. No.: 09/774,621

(22) Filed: Feb. 1, 2001

(65) Prior Publication Data

US 2002/0072878 A1 Jun. 13, 2002

(30) Foreign Application Priority Data

Feb. 1, 2000 (JP) .................................... 2000-024321

(51) Int. Cl.[7] .............................................. G06F 11/30
(52) U.S. Cl. ....................................................... 702/183
(58) Field of Search .................... 702/183, 38; 607/30; 342/457, 460; 340/573; 600/534; 360/78; 205/705, 777; 324/700, 693, 71, 72, 541; 310/301; 250/573, 226; 740/635, 647, 650; 361/126, 127, 132

(56) References Cited

U.S. PATENT DOCUMENTS

| | | | | |
|---|---|---|---|---|
| 4,806,849 A | * | 2/1989 | Kihira et al. | 324/700 |
| 4,866,393 A | * | 9/1989 | Iwai et al. | 324/549 |
| 4,980,645 A | * | 12/1990 | Soma et al. | 324/541 |
| 5,221,893 A | * | 6/1993 | Kondou et al. | 324/693 |

FOREIGN PATENT DOCUMENTS

JP        7-225777        8/1995

* cited by examiner

*Primary Examiner*—Tung S. Lau
(74) *Attorney, Agent, or Firm*—Oblon, Spivak, McClelland, Maier & Neustadt, P.C.

(57) ABSTRACT

A deterioration diagnosis method, wherein the amount of weight loss of a metallic material due to corrosion in atmospheric air for the exposure days is formulated as a function for environmental assessment points which represents a level of a harmfulness of the atmospheric conditions; and the life span of the metallic material is diagnosed based on the corrosion loss calculated from the function.

50 Claims, 18 Drawing Sheets

| Atmospheric environment Zone | | | I | | II | | III | | IV | | V | |
|---|---|---|---|---|---|---|---|---|---|---|---|---|
| Environmental factors | | | Measured value | Evaluation point | Measured value | Evaluation point | Measured value | Evaluation point | Measured value | Evaluation point | Measured value | Evaluation point |
| Temperature(°C) | | A | ≦20 | 1 | ≦25 | 2 | ≦30 | 4 | ≦35 | 8 | >35 | 12 |
| Relative humidity (%RH) | | B | ≦60 | 1 | ≦65 | 6 | ≦70 | 12 | ≦80 | 24 | >80 | 36 |
| Corrosive gas (mdd) | $SO_2$ $SO_3$ | C1 | ≦0.02 | 1 | ≦0.05 | 4 | ≦0.2 | 8 | ≦0.5 | 16 | >0.5 | 24 |
| | $H_2S$ | C2 | ≦0.02 | 1 | ≦0.05 | 6 | ≦0.2 | 12 | ≦0.5 | 24 | >0.5 | 36 |
| | $NO_2$ | C3 | ≦0.02 | 1 | ≦0.05 | 3 | ≦0.2 | 6 | ≦0.5 | 12 | >0.5 | 18 |
| | $Cl^-$ | C4 | ≦0.02 | 1 | ≦0.05 | 7 | ≦0.2 | 14 | ≦0.5 | 28 | >0.5 | 42 |
| | $NH_3$ | C5 | ≦0.02 | 1 | ≦0.1 | 3 | ≦1.0 | 6 | ≦10 | 12 | >10 | 18 |
| Sea salt particle (mdd) | | | ≦0.01 | 1 | ≦0.03 | 5 | ≦0.1 | 10 | ≦0.3 | 20 | >0.3 | 30 |
| Sea salt particle | Distance from coast (km) | D | >2.0 | | ≧1.5 | | ≧1.0 | | ≧0.5 | | <0.5 | |

FIG.2

Corrosion loss rate=(thickness of corrosion/thickness of the conductor) ×100

| IC type | Year | Manufacturer | Sealing resin | Chip protective film | Other... | Correlation function(W) |
|---|---|---|---|---|---|---|
| IC1 | 1982 | T Inc. | Epoxy blend--- | PSG | | $I_1(W)$ |
| IC2 | 1979 | N Inc. | Epoxy blend--- | None | | $I_2(W)$ |
| IC3 | 1992 | T Inc. | Epoxy blend--- | SiN | | $I_3(W)$ |
| ... | | | | | ... | |

FIG.13

| IC type | Year | Manufacturer | Sealing resin | Chip protective film | Other... | Change of time sequence of aluminium wiring corrosion area rate $U_i = h_i(t)$<br>Correlation function $F(u)$ of aluminium wiring corrosion area rate and faults |
|---|---|---|---|---|---|---|
| IC1 | 1982 | T Inc. | Epoxy blend--- | PSG | | $U_1 = m_1(t), F_1 = n_1(u)$ |
| IC2 | 1979 | N Inc. | Epoxy blend--- | None | | $U_2 = m_2(t), F_2 = n_2(u)$ |
| IC3 | 1992 | H Inc. | polyimide blend--- | SiN | | $U_3 = m_3(t), F_3 = n_3(u)$ |
| ⋮ | ⋮ | ⋮ | ⋮ | ⋮ | ⋮ | ⋮ |

FIG.14

DETERIORATION DIAGNOSTIC METHOD AND EQUIPMENT THEREOF

BACKGROUND OF THE INVENTION

1. Field of the Invention

The present invention relates to a deterioration diagnostic method and equipment thereof that will diagnose the progressive corrosion deterioration during use, the deterioration of electrical properties and, consequently, the life span, of the metallic materials, of the metallic material parts that compose electronic circuits and of the electronic circuit boards that compose electronic apparatus.

2. Description of the Related Art

First, prior art relating to diagnosis of corrosion deterioration of general metallic materials in atmosphere will be described. The effects of atmospheric temperature and relative humidity and the various types of corrosive gas and the sea salt particles present in the atmospheric environment cause chemical reactions and promote corrosion in metallic materials used in an atmospheric environment. The atmospheric environments in which metallic materials are used are multifarious. There are various kinds of environment such as environments in which temperature and humidity are controlled and hardly any corrosive gases or sea-salt particles are present, like clean rooms, environments with high hydrogen sulfide gas concentrations, like geothermal power stations, and environments close to the seashore where sea-salt particles are always in the air. Moreover, corrosion-resistive performances in atmospheric environments also vary depending on the type of metallic material.

In the past, the method adopted for the diagnosis of corrosion deterioration of metallic materials used in atmospheric environments was to expose the metallic material that was the subject of diagnosis for a specified period in the environment in which it was to be used, retrieve the material and measure the corrosion loss, find the corrosion speed from the exposure period and the corrosion loss, and estimate the life expectancy (life span or duration of life). However, since, with the corrosion of metals, there is a tendency for the corrosion speed to reduce with the passage of time, differences will arise in the corrosion speed depending on the period of exposure of the metal. There are also differences according to the season (summer or winter) in which exposure is commenced. Thus, to estimate the corrosion progress of a metal with good accuracy, long-term exposure tests using a number of exposure periods were mandatory. Also, there was the problem that, each time the value of even one factor of the environment changed there would be a requirement to carry out exposure tests of the metal.

Moreover, a method has also been adopted of diagnosing the corrosion life of a metallic material by carrying out corrosion tests of the metallic material using accelerated test equipment that simulates acceleration of the atmospheric environment, and multiplying the life span by the acceleration factor of the accelerated test. However, it is difficult to simulate an actual atmospheric environment as an accelerated test, and the accuracy of the acceleration factor was poor because of differences between environmental factors and set conditions, and thus accurate diagnosis of the life of a metallic material was very difficult.

Furthermore, a system of classifying an environment and assigning evaluation points to each environmental factor according to the range of its measured values, totalling the assessment points of the various environmental factors, and judging the environment by the total assessment points has been adopted by Computer Installation Environmental Standard for Industry JEIDA-29-1990 of the Japanese Electronic Industry Development Association. However, this is strictly only used for dividing environments into classes and cannot be applied to assessing the deterioration state of a metal or diagnosing its life.

As described above, with prior art, to perform diagnosis of the corrosion state and the deterioration state of a metallic material that was used in an atmospheric environment, or the diagnosis of its corrosion life, long-term metallic material exposure tests had to be carried out in each case. This took a vast amount of time and expense and, moreover, high-accuracy life diagnosis was not possible.

Next, prior art relating to the diagnosis of the deterioration of electrical properties through corrosion of the metallic material parts that compose electronic circuits used in atmospheric environments will be described. With an electronic circuit board used in an atmospheric environment, the metallic materials that compose the electronic circuit, such as for instance the copper of the wiring material, the steel of integrated circuit lead terminals, soldered parts and the metal-plating of contact terminals, corrode due to the effects of environmental factors in the atmosphere, such as for instance temperature, humidity, various types of corrosive gases and sea-salt particles. If the influence exerted on the metallic materials by the environmental factors is great, the corrosion of the relevant parts of an electronic circuit board will be severe, electrical malfunctions will occur, such as wiring breaks, insulation drops or short-circuits due to migration, and contact damage, and the board's life will end. The following two items of prior art relate to assessment of the deterioration due to migration out of the above. First, Japanese Laid-Open Patent Publication No. Heisei 6(1994)-11530 Gazette, "Assessment Method and Equipment for the Insulation Reliability Life of Electronic Parts", concerns a method of assessing the lives of printed wiring boards, electronic parts and the like from their insulation reliability and, in particular, proposes a good life assessment method for performing early diagnosis of life due to migration deterioration. It is a method of measuring insulation resistance or leak currents as initial and last-off dielectric characteristics, and judging the life from the time-wise variation of those characteristics.

Next, Japanese Laid-Open Patent No. Heisei 7(1995)-249840 Gazette, "A Printed Board and Method of Diagnosing Its Deterioration", proposes a method for the quantitative diagnosis of deterioration such as corrosion in printed boards and short-circuits caused by migration. It is a deterioration diagnosis method of pre-printing a pair of electrode conductors for deterioration diagnosis on a printed is board, measuring the dielectric tangent factor in the low-frequency domain between the two electrode conductors, and estimating the time to occurrence of a short-circuit between the two electrode conductors based on the value of that dielectric dissipation factor.

Since the conductor widths of conductors on electronic circuit boards in the past were broad, there were often cases when there was corrosion of the conductors due to the effect of atmospheric environmental factors but insulation deterioration due to migration and the like occurred first, and then corrosion of the conductors progressed and led to breaks in conductors. The prior art insulation deterioration diagnostic method described above was effective with the deterioration of this type of electronic circuit board. However, in recent years, narrowing of electronic circuit board conductors has progressed and there are many cases in which conductors break before insulation deterioration due to migration occurs. Thus, the above deterioration and life diagnostic method is no longer appropriate for forecasting conductor breakages. Therefore, in the case of forecasting conductor breakage life, a method was produced in which a conductor part of the relevant electronic circuit board was cut and, by observing the cross-section of the conductor, the remaining life was estimated from the remaining conductor thickness. For that purpose, a working item was taken as the product and, because it was a destructive test, a new electronic circuit board had to be adjusted and supplied in place of the board taken.

As used herein, the term "migration" means the phenomenon of migration of metallic atoms produced by electrolysis.

This is the phenomenon that, when an electric field is applied between metals under conditions of high humidity, the metal of the electrode on the high-potential side is ionized (phenomenon similar to electrolysis in water), and migrates towards the metal of the electrode on the low-potential side, ultimately creating a short circuit between the electrodes. Migration occurs more rapidly with increased humidity, increased DC electrical field, and increased contamination of the circuit board surface. That is, migration becomes more likely to occur as leakage current between the metal electrodes is facilitated. The migration that is here referred to is migration of solder in the area where the component leads are mounted on an electronic circuit board and/or migration of copper of the adjacent wiring pattern.

Moreover, for life assessment of electronic circuit parts other than electronic circuit boards, a method was used of assessing the lives of the electronic parts on a printed circuit board that composed a equipment by removing the individual parts from the board, carrying out accelerated deterioration tests, and measuring their specialized electrical characteristics. In the case of the former, failure judgements are performed by applying deterioration stress and confirming the performances of the parts. Then, the progression of cumulative failure rates for accelerated test times are deduced for each of the various types of parts, and the life point is defined at the desired cumulative failure rate An example of this is Japanese Laid-Open Patent No. Heisei 10(1998)-313034 Gazette. With this, in the case of assessing the life of a resin-sealed type IC, the IC resin package that has been removed from the board is unsealed and the corrosion state of the aluminium wiring on the IC chip inside is observed. Thus, early detection of corrosion and quantitative remaining life assessment of ICs that display defective logic or malfunctions is achieved by image measurement of the corrosion area percentage of the aluminium wiring. Also, as an example of the latter, in the case of the silver contacts that compose an electronic circuit, corrosion films are formed on the silver contact surfaces through the effects of atmospheric environmental factors and contact resistance increases and defective contact occurs. Therefore an electronic part, having silver contacts, that has been used in the relevant environment is removed, and the deterioration state of that part is judged by measuring the contact resistance of that part.

Next, the diagnosis of progressive electrical characteristic deterioration during use due to soiling of electronic circuit board surfaces will be described for electronic circuit boards that compose electronic apparatus. When electronic circuit boards are used in an atmospheric environment, dust floating in the atmosphere adheres to their surfaces and accumulates with time. Since various corrosive gases and sea salt particles present in the atmospheric environment adsorb such dust, if the humidity becomes high, ionic substances (e.g. such as chlorine ions, sulfuric acid ions, nitric acid ions and sodium ions) will ionically dissociate to become the cause of reduced insulation of the electronic circuit board surface and corrosion of the conductor pattern metals. In particular, since dust will accumulate locally on electronic circuit boards in control panels that are forcibly cooled by using fans, there will be many instances of insulation reduction and conductor pattern breakage phenomena in the short term. In such cases also, the technique of destroying part of the circuit on the board is often adopted for studying the insulation resistance values and conductor pattern corrosion states on soiled electronic circuit boards.

In the above way, in order to diagnose the various types of deterioration concerned in the corrosion of, and the lives of, metallic material parts that compose electronic circuit boards and to study the insulation resistance values and conductor pattern corrosion states of soiled electronic circuits, part or all of the relevant circuits or parts must be removed. In other words, it is essential to carry out destructive testing of the circuits or parts. This not only requires a great deal of labor and expenditure but, with this method there is the great problem that, even if, as a result of diagnosis, it is confirmed that the remaining life of the equipment is satisfactory, that equipment cannot be re-used after diagnosis, and it will be necessary freshly to adjust an electronic circuit and assemble it into the electronic apparatus.

Also, there were methods of measuring heat distribution as methods of deterioration diagnosis of electronic circuit boards. However, to measure heat distribution, it was necessary to remove the electronic circuit board, and measure the heat distribution of the board as a whole by freshly inputting a power source. As an example of this, there is Japanese Laid-Open Patent No. Heisei 11(1999)-14576 Gazette, "Deterioration Diagnosis and Equipment for Mounting Boards". With this, the temperature distribution until the surface temperature of the mounting board achieves the steady state after power source input is measured, and the temperature-rise image data that have been converted to images are compared with past temperature-rise image data. The amount of variation of temperature distribution between the two is calculated, and when this value exceeds a pre-set threshold there is judged to be deterioration. With this method, there is no need to destroy the electronic circuit board but specialised analysis equipment for thermal distribution images is required.

With prior art there were such problems as the following. Exposure testing of metallic materials over a long period was indispensable for the diagnosis of the corrosion, deterioration state and corrosion life of metallic materials used in atmospheric environments. Also, for the diagnosis of the corrosion states of the various types of electrical characteristics concerned in the corrosion of metallic material parts that compose electronic circuits, and for the diagnosis of the corrosion states and insulation deterioration states of electronic circuit boards that compose electronic apparatus, those electrical characteristics could only be tested by partial or complete withdrawal and destructive testing of those metallic material parts and electronic circuit boards. Moreover, those parts and boards could not be re-used after diagnosis. Furthermore, although diagnosis by thermal distribution imaging was non-destructive, specialized diagnostic equipment was required, and it was not suitable for general use.

SUMMARY OF THE INVENTION

Accordingly, one object of the invention in the present application, which is designed in the light of the above, is to provide a novel deterioration diagnostic method and associated equipment thereof that can diagnose the life of a metallic material without requiring exposure testing of the metallic material over a long period;

can, for metallic material parts that compose an electronic circuit, diagnose the corrosion state of the metallic material parts without requiring withdrawal of the electronic circuit and performance of destructive testing; and can diagnose the life of electronic apparatus without requiring withdrawal of electronic circuit boards and performance of destructive testing.

In order to solve the above problems, the purport of the deterioration diagnostic method of the invention in the present application is to formulate the quantities of corrosion loss of metallic materials for numbers of exposure days in atmosphere as environmental assessment point functions that indicate degrees of harmfulness of atmospheric environments, and to diagnose the lives of the metallic materials on the basis of the quantities of corrosion loss found from these functions. Using this composition, the state of progression of corrosion loss of the relevant metallic material in an atmospheric environment, that is to say a function of the number of exposure days and the quantity of corrosion loss, is obtained by measuring and assessing atmospheric environmental assessment points of atmospheric environments, and the life of that metallic material in the relevant atmospheric environment is diagnosed.

Moreover, the corrosion diagnostic method of the invention in the present application formulates the corrosion rate of a metallic material in an atmospheric environment as an environmental assessment point function that indicates the degree of harmfulness of the relevant atmospheric environment, and diagnoses the life of the metallic material on the basis of the corrosion rate found from this function. Using this composition, the corrosion rate of the relevant metallic material in an atmospheric environment is obtained by measuring and assessing the environmental assessment points of the atmospheric environment, and the life of that metallic material in the relevant environment is diagnosed.

Furthermore, corrosion diagnostic equipment of the invention in the present application possesses:

an input means (unit) that inputs each environmental factor quantity that is measured by an environmental factor quantification means (unit);

a first database that stores functions that provide relationships between the quantity of each environmental factor and each factor by factor assessment point;

a second database that stores functions that provide relationships between environmental assessment points for each type of metallic material and each factor by factor assessment point;

a factor by factor assessment point calculation means (unit) that computes each factor by factor assessment point using the said functions read from the first database and the various environmental factor quantities inputted from the input means (unit);

an environmental assessment point calculation means (unit) that computes environmental assessment points that express degrees of harmfulness of atmospheric environments using the functions read from the second database and the various factor by factor assessment points that are computed by the factor by factor assessment point calculation means (unit);

a corrosion loss calculation means that computes the relationships between the corrosion losses of metallic materials in atmospheric environments and the number of exposure days, using the functions formulated by taking the environmental assessment points computed by this environmental assessment point calculation means (unit) as parameters;

a corrosion rate calculation means (unit) that computes corrosion rates of metallic materials in atmospheric environments using the functions formulated by taking the environmental assessment points computed by the environmental assessment point calculation means (unit) as parameters;

a corrosion loss correction calculation means (unit) that computes corrections for the relationships between corrosion losses and number of exposure days, which are computed by the corrosion loss calculation means (unit), based on the corrosion losses of metallic materials in the number of exposure days of a specified period;

a corrosion rate correction calculation means (unit) that computes corrections for the corrosion rates, which are computed by the corrosion rate calculation means (unit), based on the corrosion losses of metallic materials in the number of exposure days of a specified period;

a remaining life calculation means (unit) that calculates the remaining lives of metallic materials on the basis of the relationships between corrosion loss and number of exposure days corrected by the corrosion loss correction calculation means (unit) or the corrosion rates corrected by the corrosion rate correction calculation means (unit); and an output means (unit) that outputs the metallic material by metallic material remaining lives that are calculated by this remaining life calculation means (unit) as diagnosis results.

Using this composition, by inputting measured values for the quantities of each environmental factor, a series of computations are carried out that include computing factor by factor assessment points for each of the various environmental factors, computing environmental assessment points for atmospheric environments, computing the relationships between the corrosion losses of metallic materials and the numbers of exposure days in the atmospheric environments of those environmental assessment points, computing the corrosion rates of metallic materials in the atmospheric environments of those environmental assessment points, computing corrections for the relationships between corrosion losses and numbers of exposure days, computing corrections for corrosion rates and calculating remaining lives of metallic materials are carried out, and those remaining life diagnosis results are outputted.

Still further, deterioration diagnosis equipment of the invention in the present application possesses:

a degree of soiling (contamination level or pollution level) measurement means (unit) that measures the degrees of soiling and the soiling rates of electronic circuit board surfaces;

a deterioration index database that stores the correlation functions between degrees of soiling of electronic circuit boards and deterioration indices;

a deterioration index value calculation means (unit) that calculates deterioration index values corresponding to the degree of soiling measured values from the degree of soiling measured values outputted from the degree of soiling measurement means (unit) and correlation functions read from the said deterioration index database;

a life database that stores life threshold values of deterioration indices for electronic circuit boards;

a differential (deviation) degree of soiling calculation means (unit) that calculates differential degrees of soiling, that are equivalent to the differences between the existing deterioration index values and life threshold values read from the life database, from the correlation functions read from the deterioration index database; and a remaining life calculation means (unit) that calculates remaining lives by dividing the differential degrees of soiling calculated by this differential degree of soiling calculation means (unit) by the soiling rates outputted from the degree of soiling measurement means (unit).

Using this composition, the degree of soiling and the soiling rate of an electronic circuit board surface are measured; the deterioration index value corresponding to this degree of soiling measured value is calculated; the differential degree of soiling from the existing deterioration index value and its life threshold value is calculated and calculation of the remaining life of the electronic apparatus is performed from this differential degree of soiling and the soiling rate measured value.

BRIEF DESCRIPTION OF THE DRAWINGS

A more complete appreciation of the present invention and many of the attendant advantages thereof will be readily obtained as the same becomes better understood by reference to the following detailed description when considered in connection the accompanying drawings, wherein:

FIG. 2 is the factor by factor assessment point table divided into classes by quantity of environmental factor in the above first embodiment;

FIG. 13 is a table to illustrate the detail of the corroded area percentage database in the above third embodiment;

FIG. 14 is a table to illustrate the detail of the life diagnosis database in the above third embodiment;

DETAILED DESCRIPTION OF THE PREFERRED EMBODIMENTS

Figure 1:
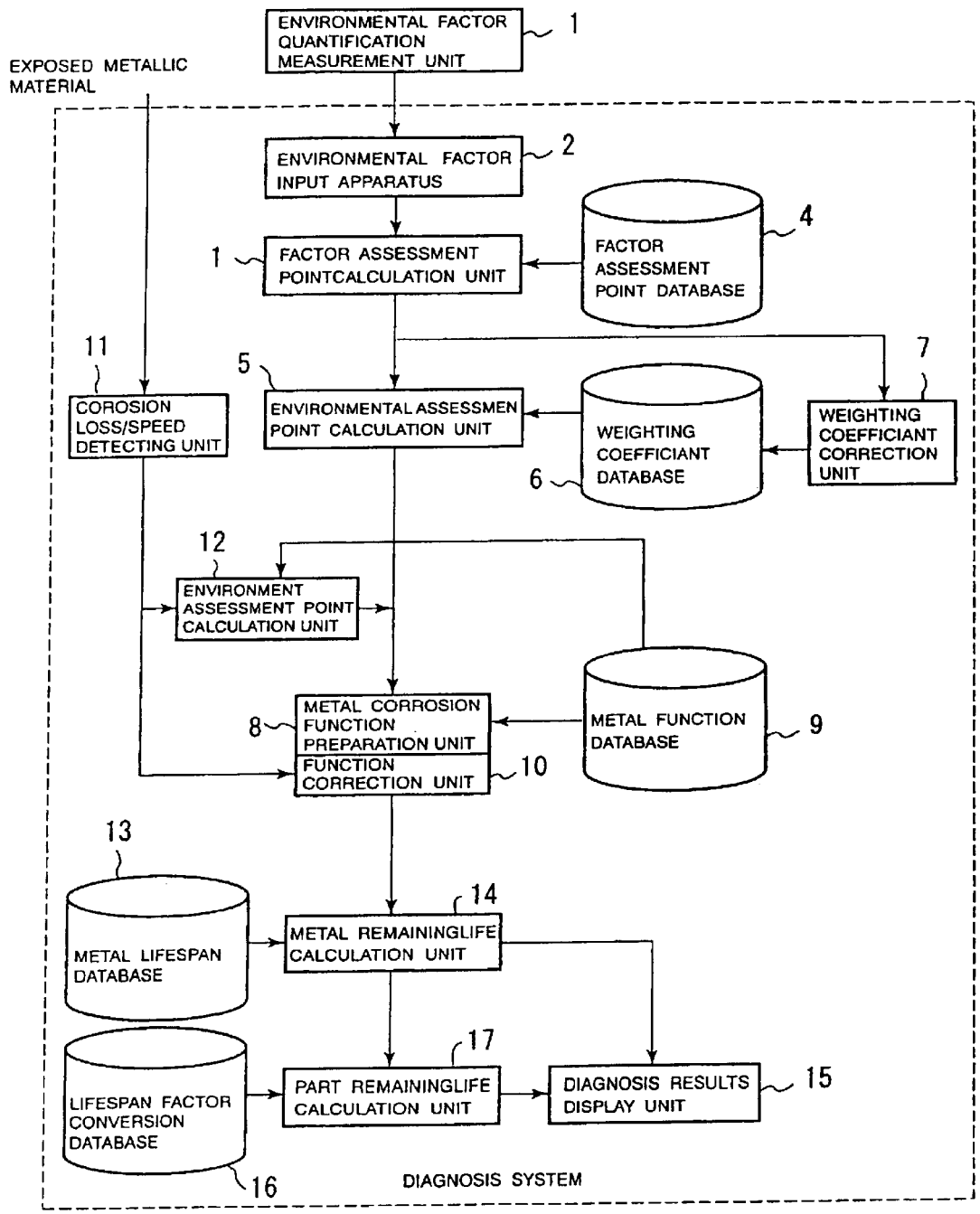
FIG. 1 is a block diagram of deterioration diagnostic equipment that is a first embodiment of the invention in the present application.

Referring now to the drawings, wherein like reference numerals designate identical or corresponding parts throughout the several l views, and more particularly to FIG. 1 thereof, one embodiment of the present invention will be described.

FIG. 1-FIG. 8 are drawings showing a first embodiment of the present invention. First, the composition of the deterioration diagnostic equipment of this embodiment will be described using FIG. 1. In the drawing, numeral 1 is an environmental factor quantification measurement means (unit) that measures the relevant atmospheric environment and includes various types of corrosive gas concentration meters, a thermometer, a relative humidity meter (that is to say, humidity meter or hygrometer) and a sea salt particle measurement means. The quantities of environmental factors are measured by placing each measurement means (unit) in the relevant atmospheric environment for 1–3 months. Temperature and relative humidity are measured by a temperature and humidity meter fitted with automatic memory equipment, and mean temperature and mean humidity are found. The gas concentrations of corrosive gases are measured by continuous gas concentration measurement apparatus for each separate corrosive gas. The mean gas concentrations (ppm) are found and, by exposing alkaline filter papers and acidic filter papers in the relevant atmospheric environment for fixed periods, the gas adsorption quantities (mdd) that are adsorbed to the filter papers are found. For sea salt particles, the quantity of sea salt particles (mdd) is found by the gauze collection method, and the distance of the relevant atmospheric environment from the coast (km) is found. The size of the alkaline filter papers and acidic filter papers used in corrosive gas measurement is small (papers of width 5 cm and length 13 cm are normally used) and there are no restrictions on exposure sites. Therefore it is desirable that they should be exposed as close as possible to the electronic apparatus or the like that is the subject of diagnosis. By this means, more accurate measurement of the environmental factor quantities of the atmospheric environment to which the subject of diagnosis is exposed will be possible.

The various factor quantities measured with environmental factor quantification means (unit) 1 are inputted by environmental factor quantity input equipment 2 as the environmental factor quantity input means(unit), and are sent to factor by factor assessment point calculation unit 3 as the factor by factor assessment point calculation means (unit). Factor by factor environmental assessment point calculation unit 3 uses the outputs of environmental factor quantity input equipment 2 to calculate the factor by factor assessment points. Factor by factor assessment point calculation unit 3 reads the data showing factor quantities and their relationships with factor by factor assessment points from factor by factor assessment point database (the first database) 4, and calculates the factor by factor assessment points. In factor by factor assessment point database 4, as well as the factor by factor assessment points due to quantities of classified environmental factors, are stored the functions for calculating the factor by factor assessment points by using the environmental factor quantities. The stored functions also include functions that interpolate between the value of a classified class and the middle value of the environmental factor quantity of that class.

Numeral 5 is an environmental assessment point calculation unit as the environmental assessment point calculation means (unit). This reads the factor by factor weighting coefficients from factor by factor weighting coefficient database (the second database) 6 for each factor by factor assessment point calculated by factor by factor assessment point calculation unit 3, and calculates the environmental assessment points by the sums of the products of each factor by factor assessment point and each factor by factor weighting coefficient. A weighting coefficient table that is determined by combinations of metallic materials and corrosive gases is stored in factor by factor weighting coefficient database 6. Also, the data of factor by factor weighting coefficient database 6 are changed by weighting coefficient correction unit 7 that possesses the functions of setting a certain environmental factor threshold value, and of changing to another factor weighting coefficient if that threshold value is exceeded.

Metal by metal corrosion function preparation unit 8 prepares metal by metal corrosion loss functions and corrosion speed functions using the environmental assessment points calculated by environmental assessment point calculation unit 5. Each function is prepared as a function of an environmental assessment point and time. Calculation expressions for the coefficients of the metal by metal corrosion loss functions and corrosion rate functions are stored in metal by metal function database 9. Function correction unit 10 is located in metal by metal corrosion function preparation unit 8. In cases when there is a metallic material that is exposed in the relevant environment from which environmental assessment points are calculated, this unit corrects the functions prepared by metal by metal corrosion function preparation unit 8 using the corrosion losses and corrosion rates detected by corrosion loss/corrosion rate detection means (unit) 11. Numeral 12 is an environmental assessment calculation point unit and, when the corrosion loss and corrosion rate of a given metal are calculated by corrosion loss/corrosion rate detection means 11, calculates the environmental assessment point from the metal's corrosion function that is stored in metal by metal function database 9 and the values of the corrosion loss and exposure time of the metal. When environmental factor quantification means (unit) 1 is not used, environmental assessment point calculation unit 12 can find the environmental assessment point from the exposure results (exposure period, corrosion loss) for a given metal.

Metal by metal remaining life calculation unit 14, as the remaining life calculation means (unit), computes the remaining life of a metal using the corrosion loss function and the corrosion rate function for the metal that are prepared by metal by metal corrosion function preparation unit 8. The corrosion loss critical values and corrosion rate critical values for each metal are stored in metal by metal remaining life database 13, and are used as threshold values by metal by metal remaining life calculation unit 14. The calculated metal by metal remaining lives are displayed as diagnosis results for metal materials by diagnosis result display unit 15 that is the output means (unit). Also, for parts that are composed of a plurality of metals, a remaining life is calculated for each separate metal. Then, the life of the metal that will soonest reach the end of its life out of the metals used in the part is calculated as the remaining life of the part, and is displayed as the diagnosis result for the part by diagnosis result display unit 15. 16 is a life factor conversion database and stores functions for converting the corrosion losses and conversion rates of metals to physical quantities that directly contribute to the lives of parts and their life judgement threshold values. Part remaining life calculation unit 17 performs the conversion from metal by metal corrosion functions to physical quantities that directly contribute to the lives of parts, using the data of life factor conversion database 16, and calculates the remaining lives of parts. The calculated results are displayed as remaining life results for parts by diagnosis result display unit 15.

A corrosion loss calculation means (unit) and a corrosion rate calculation means (unit) are contained in the above metal by metal remaining life calculation unit 14. The corrosion loss calculation means performs calculation of corrosion losses, using the metal corrosion loss functions that are prepared by metal by metal corrosion function preparation unit 8. The corrosion rate calculation means performs calculation of corrosion rates, using the metal corrosion rate functions that are prepared by metal by metal corrosion function preparation unit 8. Also, a corrosion loss correction calculation means (unit) and a corrosion rate correction calculation means (unit) are contained in function correction unit 10. The corrosion loss correction calculation means (unit) performs correction calculation for metal corrosion loss functions, using exposed metallic material corrosion losses selected from corrosion loss/corrosion rate detection means (unit) 11. The corrosion rate correction calculation means (unit) performs correction calculation for metal corrosion rate functions, using exposed metallic material corrosion rates selected from corrosion loss/corrosion rate detection means (unit) 11. The deterioration diagnostic equipment is composed by the composition elements from 1 to 15 stated above.

FIG. 2 shows the factor by factor assessment points by quantity of classified environmental factor of factor by factor assessment point database 4. This is divided into five classes according to quantity of environmental factor, and factor by factor assessment point calculation unit 3 can obtain assessment points factor by factor according to the measured quantities of the environmental factors by consulting this table. The environmental factors that are measured are the principal environmental factors that affect the degree of corrosion of metallic materials:—temperature, humidity, corrosive gases (sulphur group gases such as $SO_2$ and $H_2S$, nitrogen oxide gases such as $NO_2$, chloride gases such as $Cl_2$ and HCl, and $NH_3$ gas), sea salt particles (quantity of sea salt particles or distance from the coast). Corrosion occurs through the combined action of the environmental factors. However, since this interaction is complex, each environmental factor is classified and determination of assessment points is performed for each separate environmental factor. The bases for classification and assessment points are the measured values of each environmental factor of several hundred different locations in the Japanese homeland field and the results of investigating the corrosion of metallic materials exposed in those environments. Environmental assessment points that take into consideration all the environmental factors of atmospheric environments can be found by finding and totalling the assessment points for each separate environmental factor of those environments, and the corrosivity of the atmospheric environments can be objectively judged by the numerical values of the environmental assessment points. As a result, it is possible to diagnose with good accuracy the corrosivity of metallic materials.

Figure 3:
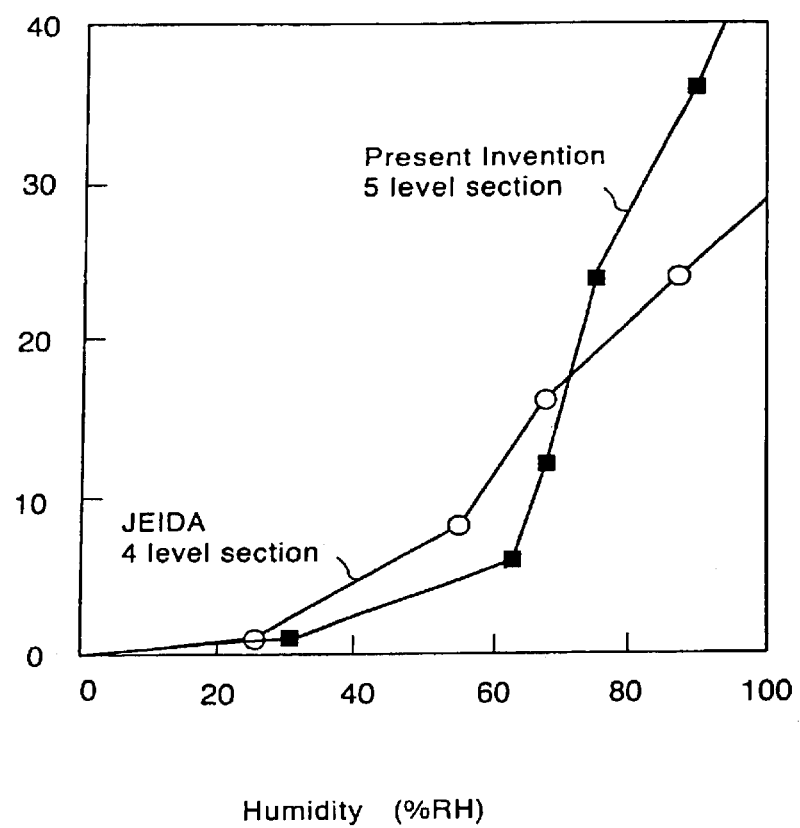
FIG. 3 is a graph to illustrate the difference between the five-stage classification for humidity in the above first embodiment and the four-stage classification of JEIDA-29-1990.
Figure 4A:
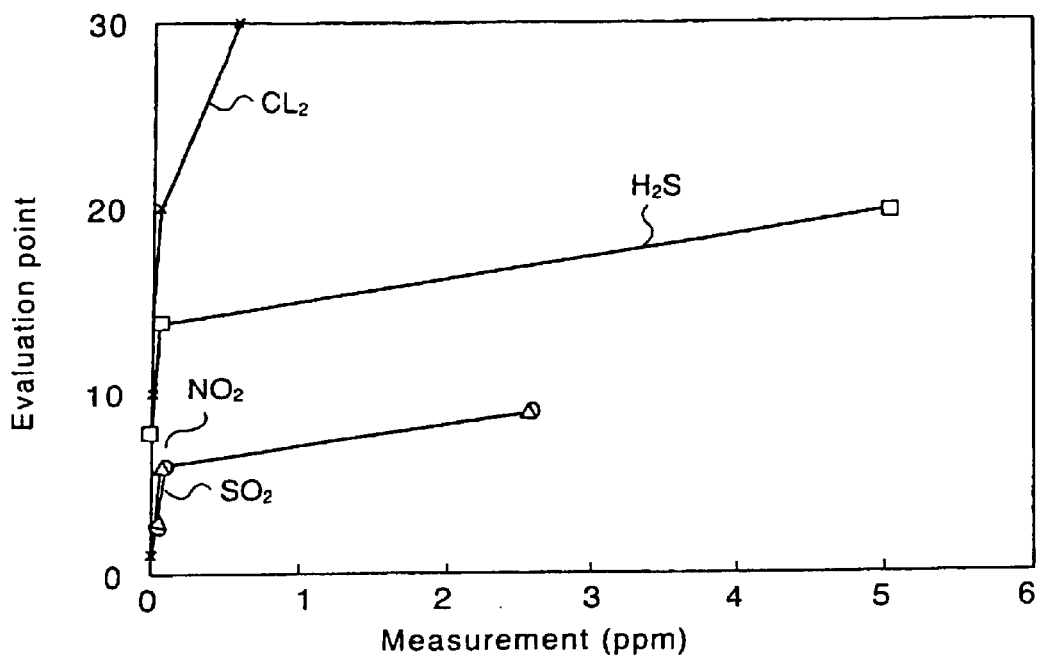
FIG. 4 is graphs to illustrate the differences between the five-stage classifications for corrosive gases in the above first embodiment and the four-stage classifications of JEIDA-29-1990.
Figure 4B:
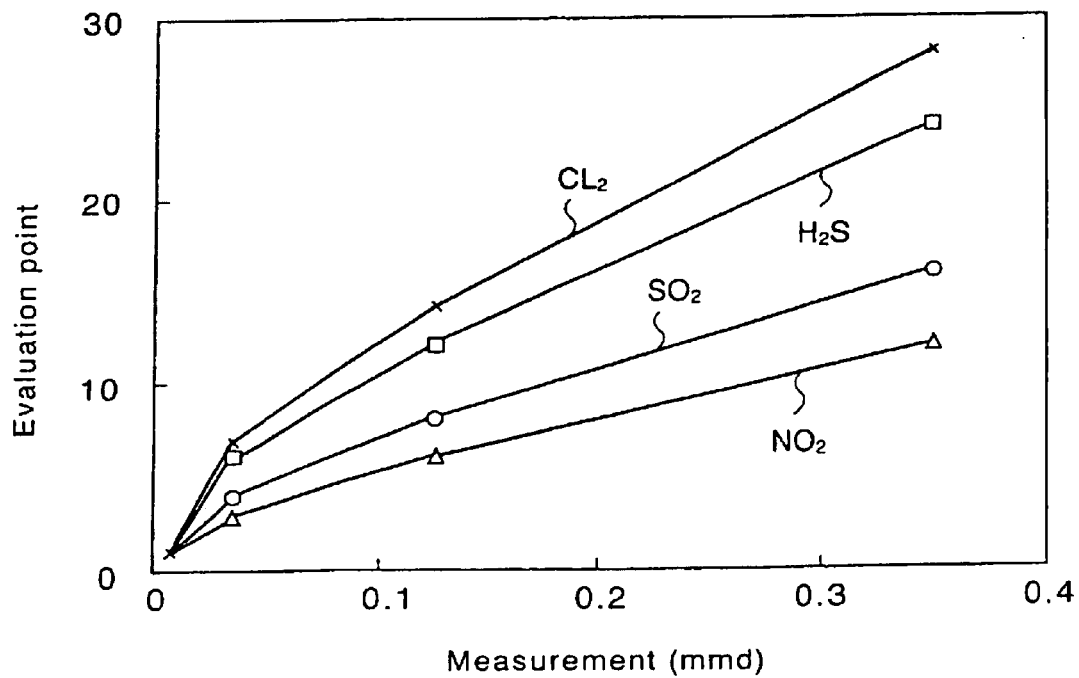

Next, the difference between the four-stage classification of Computer Installation Environmental Standard for Industry JEIDA-29-1990 of the Japanese Electronic Industry Development Association and the five-stage classification of this embodiment will be described. With JEIDA-29-1990, allotted assessment points for each separate factor are found by classifying the established values of each environmental factor in four stages, dividing the environment into five stages the by totals of those points, and displaying them as qualitative environmental corrosivities. FIG. 3 is a graph to illustrate the difference between the four-stage classification advocated by JEIDA-29-1990 and the five-stage classification of this embodiment in the case of the humidity factor. The graph shows the classified relative humidity quantity medians and the bent-line functions that pass through the factor by factor assessment points at that time. In comparison with the four-stage classification function, with the five-stage classification function of this embodiment the assessment points for humidity increase in an accelerating manner. This well reflects the fact that, in the low humidity domain, the effect of the humidity on the corrosion reactions of metallic materials is small but, the higher the humidity domain becomes, the greater the effect. To continue, the difference in the classifications of gases will be described. FIG. 4A and FIG. 4B are graphs to illustrate the difference between the four-stage classification advocated by JEIDA-29-1990 and the five-stage classification of this embodiment, shown in FIG. 2, for gases. They show the classified medians of various gases and the bent-line functions that pass through the factor by factor assessment points at that time. Although no simple comparison can be made because of the difference in the units for the detected gas quantities, the tendency of the divisions of the JEIDA-29-1990 four-stage classification is clear. This is because, in the four-stage classification, the upper limit of the measured values of the fourth class for each gas show the maximum permitted concentrations of each gas in which humans may work. Consequently, the division of actually existing environments is into the three divisions of Classes 1~3. As opposed to this, the corrosive gas classification of this embodiment divides them into five stages in the actually existing measured value range. By this means the actual environments can be more finely divided and the atmospheric environment can be accurately judged, while the accuracy of the corrosion life diagnosis of metallic materials can be improved. Consequently, it transpires that, through the use of tables classified in five stages by this embodiment, corrosion lives of metallic materials can be more accurately estimated.

Figure 5:
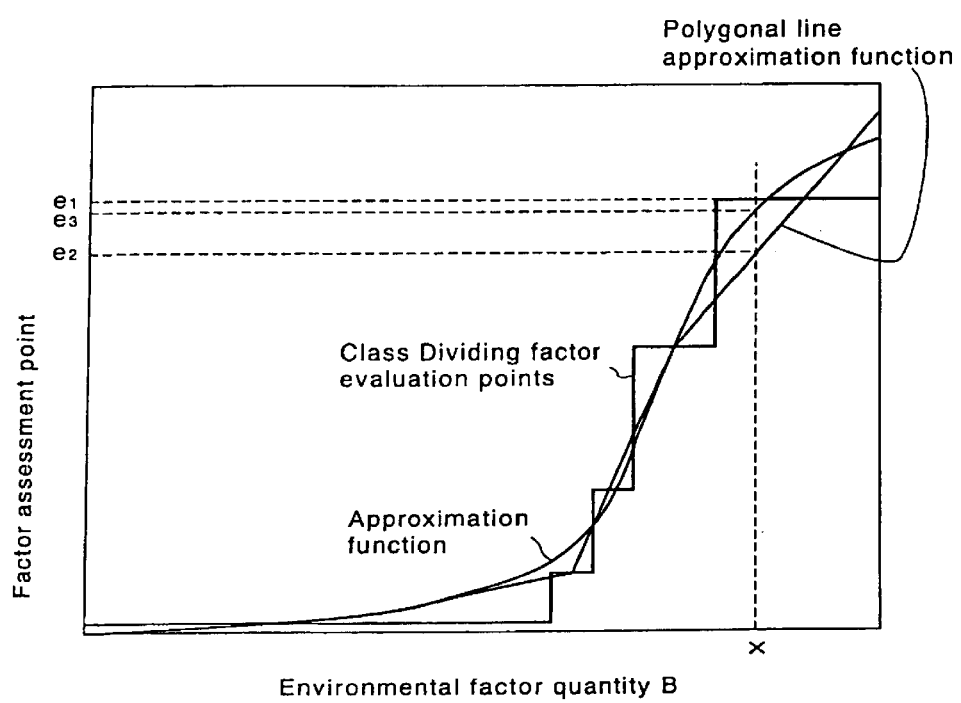
FIG. 5 is a graph showing the relationship between the quantity of an environmental factor and the factor by factor assessment points in the above first embodiment.

FIG. 5 is an example of a function that is stored in factor by factor assessment point database 4 and calculates factor by factor assessment points using environmental factor quantities. The horizontal axis shows the quantity of the environmental factor, and the vertical axis shows the factor by factor environmental assessment points. The example in the drawing shows the classified environmental factor quantity medians that are given in FIG. 2, the bent-line function that passes through the factor by factor assessment points at that time, and a function approximating to that. In factor by factor assessment point database 4 are stored classified tables, bent-line functions and approximate functions, as well as functions based on data obtained by experiments. For example, when the quantity of measured environmental factor B is x, the factor by factor assessment point from the classified table is $e_1$, the bent-line function from the classified table is $e_2$ and approximate function $e_3$ is calculated by factor by factor assessment point calculation unit 3. By using this approximate function and the bent-line function, it becomes possible more precisely to calculate the factor by factor assessment points due to the quantities of the environmental factors. Also, the calculation of more accurate environmental assessment points and the forecasting of metallic deterioration quantities become possible.

Environmental assessment point calculation unit 5 reads factor by factor weighted coefficients k from factor by factor weighting coefficient database 6 for the factor by factor assessment points e calculated by factor by factor assessment point calculation unit 3, and calculates environmental assessment points E using Expression (1).

$$E = \sum_{i=1}^{n} k_i \cdot e_i \tag{1}$$

(here, n: total number of factors)

In factor by factor weighting coefficient database 6 are stored weighting coefficients that are pre-determined by combining a metal and the dominant corrosive gas of the relevant environment. The assessment points stored in factor by factor assessment point database 4 are values that can be applied in estimating the corrosive deterioration of general metals such as copper, silver, aluminium, iron, nickel, chromium and zinc. However, in environments in which hydrogen sulfide gas is dominant, such as for example geothermal power stations and sewage treatment plants, the corrosion rate of copper is very great. Therefore, the precision of estimating the corrosive deterioration of copper with diagnosis using the assessment points stored in factor by factor assessment point database 4 will reduce.

Accordingly, in order to ameliorate such a circumstance, in the case of corrosion diagnosis of copper in a hydrogen sulfide gas environment, the weighting coefficient that multiplies the hydrogen sulfide gas factor by factor assessment points is set to an appropriate numerical value, while the other factor by factor assessment points are set at 1. The factor by factor weighting coefficients that are set for each combination of a metal and an environmental factor are similarly stored in factor by factor weight coefficient database 6.

Figure 6:
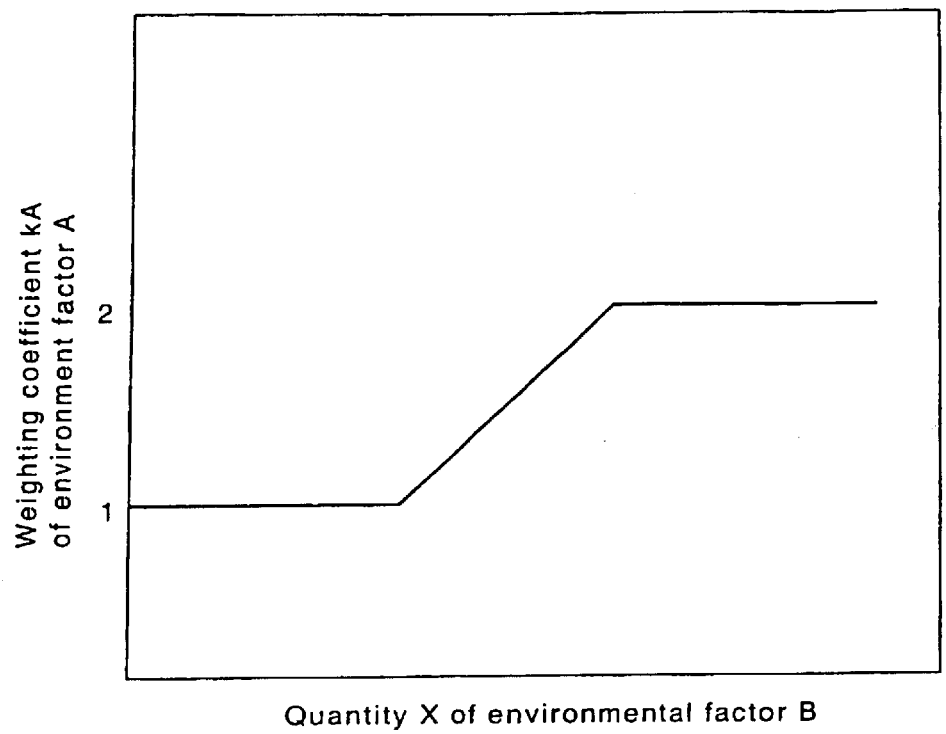
FIG. 6 is a graph showing the relationship between the quantity of an environmental factor and the environmental factor weighting coefficient in the above first embodiment.

Moreover, as well as that, factor by factor weighting coefficient database 6, using weighting coefficient correction unit 7, can correct weightings by quantity x of factors other than the factor multiplied by the weighting coefficient. For example, as shown in FIG. 6, weighting coefficient $k_A$ of environmental factor A is altered in weighting coefficient unit 7 using the quantity of another environmental factor (here, the quantity of environmental factor B). That is to say, weighting coefficient k is expressed as a function of environmental factor quantity x.

$$k_i = f(x_j) \text{ (here, } i \neq j) \tag{2}$$

Metal by metal corrosion function preparation unit 8 prepares corrosion loss functions and corrosion rate functions for different types of metals based on the environmental assessment points calculated by environmental assessment point calculation unit 5. The corrosion loss function W of a metal is prepared as a function of environmental assessment point E of the atmospheric environment in which that metal was installed (exposed) and exposure period d (number of days).

$$W = f(E, d) \tag{3}$$

The curved corrosion loss function is expressed as a linear expression of the square root of exposed time d, and the linear expression of each coefficient can be stated as a polynomial of the environmental assessment point. That is to say, when the linearly expressed coefficients are taken as α and β, the corrosion loss function of a metal can be shown by Expression (4).

$$W = \alpha(E) \cdot \sqrt{d} + \beta(E) \tag{4}$$

Figure 7:
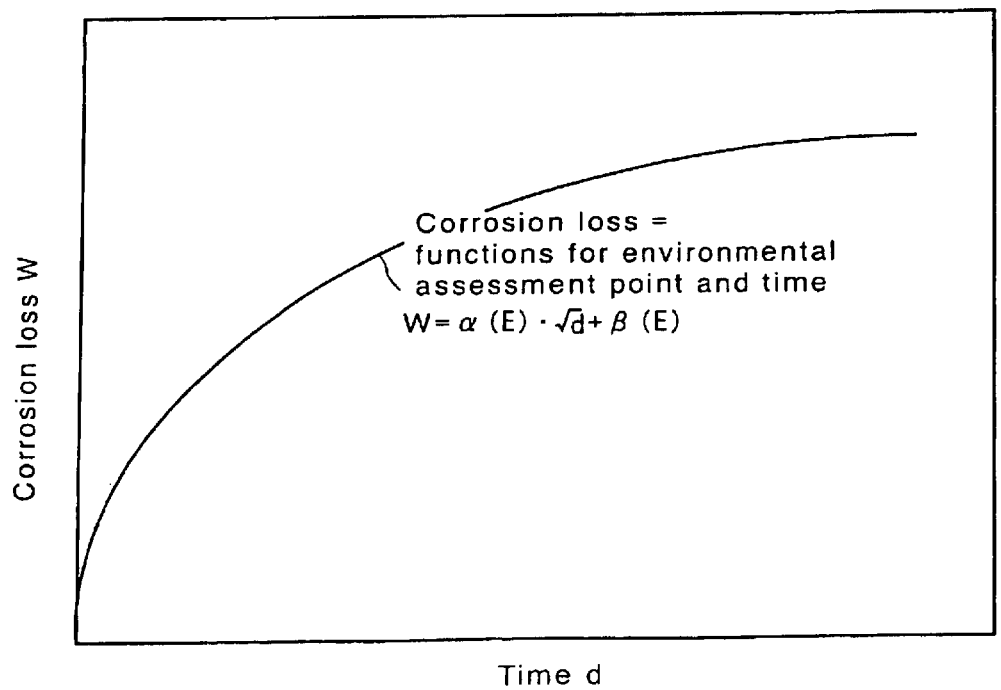
FIG. 7 is a graph showing the relationship between the corrosion loss of a metallic material and the exposure time in the above first embodiment.

FIG. 7 is a graph of the corrosion loss function W of a metal based on Expression (4) and the atmospheric environment exposure time d. For polynomial α, β for the environmental assessment point E of Expression (4), the polynomial terms and constants differ depending on the type of metal, and the metal by metal terms and constants are stored in metal by metal function database 9 Also, Expression (5), which is Expression (4) differentiated for time d, shows the corrosion rates for metals.

$$dW/dt = g(E, d) \tag{5}$$
$$= \alpha(E)^2 / (W - \beta(E))$$

Provided one knows environmental assessment point E and exposure time d, it is possible to find the corrosion loss and corrosion rate of a metal in that atmospheric environment by obtaining them from Expression (4) and Expression (5). That is to say, it is possible to estimate to what degree corrosion has progressed even without studying an exposed metal on site. Consequently it becomes possible quantitatively to express the deterioration states of metallic materials. Moreover, when there is a limiting value to corrosion loss, it is possible to estimate the period from the existing state to reaching the limiting value using the corrosion loss and corrosion rate functions, and therefore it is possible quantitatively to calculate the remaining life of a metallic material.

Figure 8:
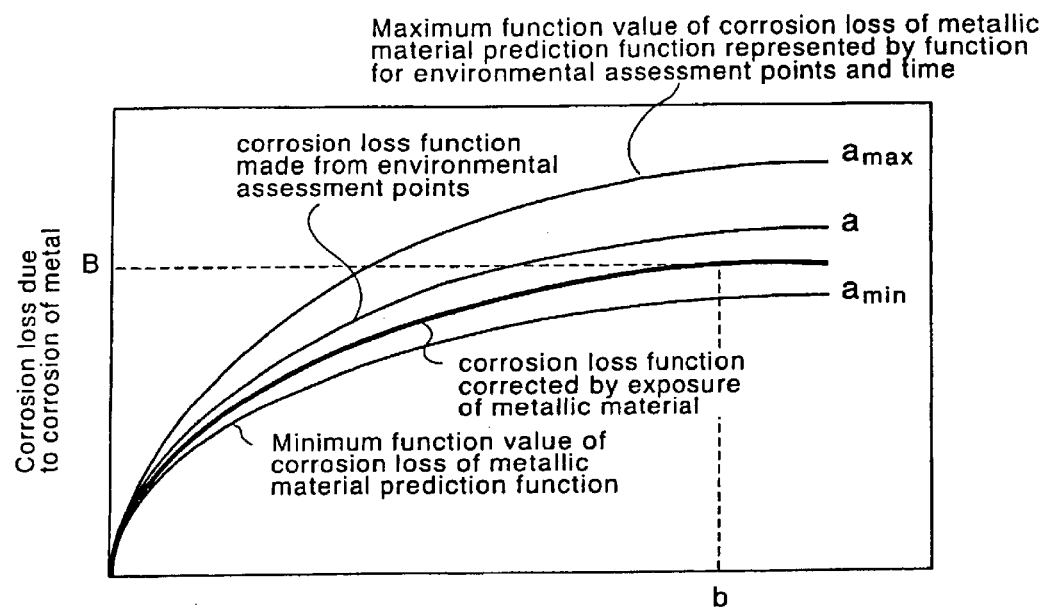
FIG. 8 is a graph to illustrate the correction method for the corrosion loss function using metallic material exposure in the above first embodiment.

FIG. 8 shows the method of correcting the corrosion loss function of a metallic material. A function prepared by metal by metal corrosion function preparation unit 8 is uniquely determined at a given environmental assessment point. Graph a in FIG. 8 is a corrosion loss function prepared using given environmental assessment point A. However, even though it may be the same environmental assessment point A and the same metal, there will be differences in the quantities of the environmental factors composing environmental assessment point A, and thus randomness will exist in the corrosion loss of the metal. In FIG. 8, this is shown as randomness range maximum value $a_{max}$ and randomness range minimum value $a_{min}$. Normally, corrosion loss of a metal will follow graph a, and for that reason the corrosion loss of the metal can be estimated using graph a. Thus, by exposing a metallic material for a specified period in the relevant environment, it is possible to grasp the relationship between the corrosion loss and the corrosion rate of a metal, and therefore it is possible to determine the metal corrosion loss function from within the randomness range. For example, if, as the result of exposing a metal, the exposure time is taken as b and the corrosion loss as B, the corrosion loss function can be corrected to the function that passes through point (b, B).

Next, the method of obtaining environmental assessment points using the metallic material corrosion losses or corrosion rates of metals that have undergone short-term exposure will be described. The corrosion loss of a metal, as shown by Expression (3), can be expressed as a function of the exposure period of the metal and the environmental assessment point of the atmospheric environment in which it was exposed. This function is stored in metal by metal function database 9. Accordingly, if the exposure loss of a metal exposed for a short term is known, the environmental assessment point can be deduced using the exposure period, the corrosion loss and Expression (3). Moreover, it is also the same using the corrosion rate and Expression (5). In this way, even without performing measurement of environmental factor quantities, it is possible to deduce environmental assessment points using corrosion loss or corrosion rate information for metals that have undergone short-term exposure. Using these deduced environmental assessment points it is possible to prepare corrosion loss functions and corrosion rate functions for other than exposed metals.

The metal life span calculation unit 14 calculates the time taken to reach a predicted amount of metal corrosion and a metal corrosion limit value using a corrosion function made at the metal corrosion function generation unit 8 and the function correcting unit 10. The metal corrosion limit value is stored at the metal life span database 13. Information such as, for example, the fact that a metal used at the outer side of a control panel is iron of a thickness of a certain number of millimeters, or to what extent an amount of metal has to be corroded by in order to become unusable is stored.

The results calculated at the metal life span calculation unit 14 are displayed on the diagnosis results display unit 15 as diagnosed results. Further, the types of metal of which the parts are composed and threshold value data showing the extent to which the metal volume has to be reduced by before the parts cease to function are also stored at the metal life span database 13. Of the metals composing the parts, the metal life span calculation unit 14 calculates the life span of a part as being the life span of the metal that is the first to expire (the metal with the shortest life span). The calculated results are displayed at the diagnosis results display unit 15.

Threshold value data for the life span of electronic parts and mechanical parts is stored at the life span factor conversion database 16. A threshold value for the life span of electronic parts and mechanical parts is not necessarily the corrosion loss and corrosion speed of a metal, and other physical values can be factors in the life span (such as corrosion area rate, film thickness, thickness of corrosion, etc.). A function for converting metal corrosion loss or corrosion speed into other life span factors are also stored at the life span factor conversion database 16. The part life span calculation unit 17 calculates life span of parts using data of the life span factor conversion database 16 and a function created at the metal corrosion function generation unit 8, and displays the results of the diagnosis at results display unit 15.

Figure 9:
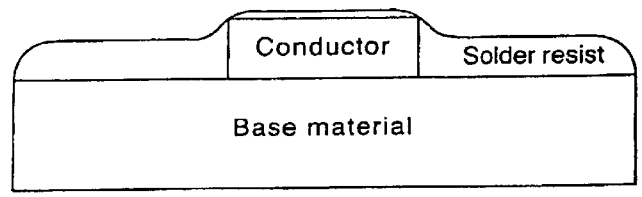
FIG. 9 is a drawing showing a conductor cross-section on an electronic circuit board in a second embodiment of the present invention.
Figure 10A:
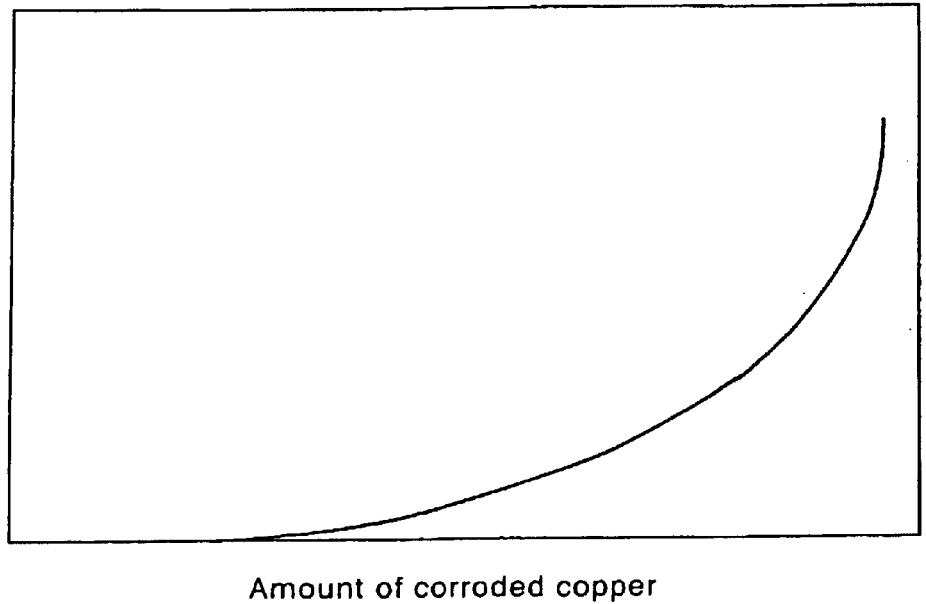
FIG. 10 is drawings showing the relationship between the corrosion thickness of a conductor and corrosion amount of copper plate exposed for the same time in the above second embodiment.
Figure 10B:
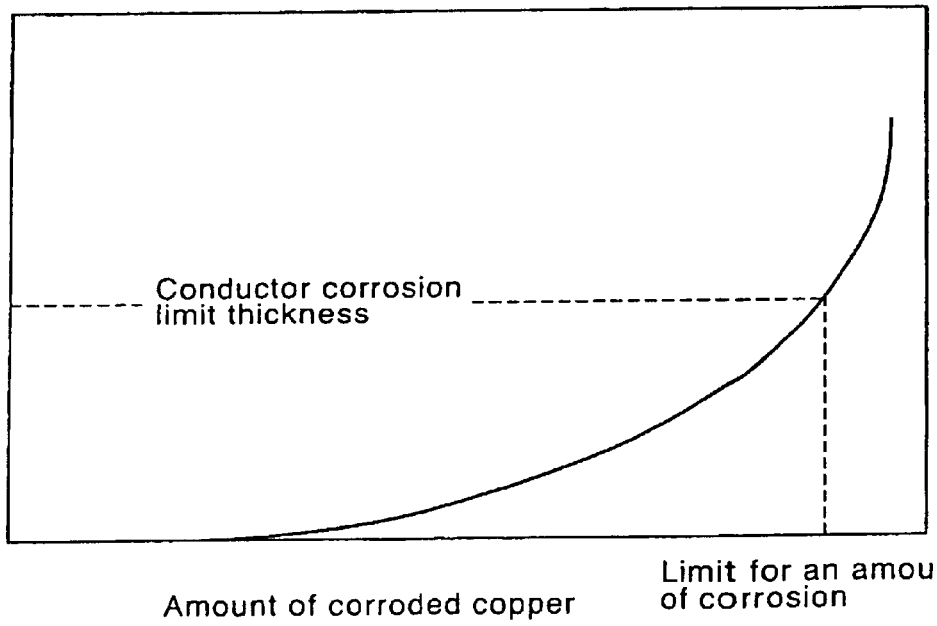
Figure 11:
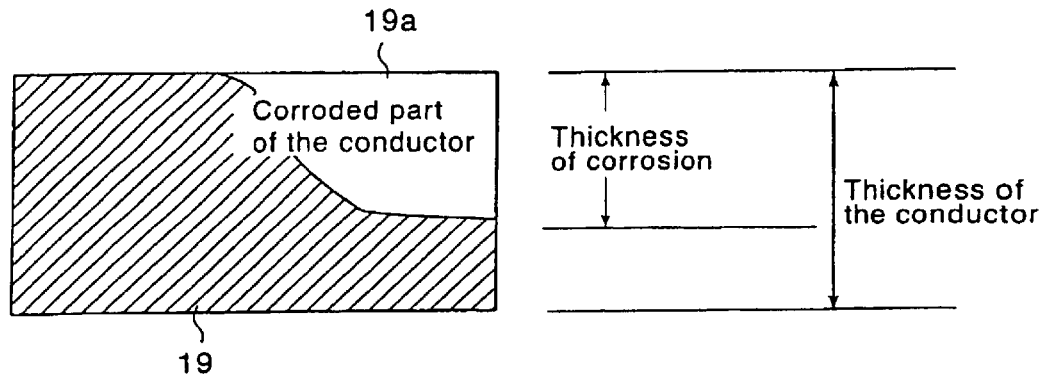
FIG. 11 is a drawing showing the cross-section of a corroded conductor in the above second embodiment.

FIG. 9 to FIG. 11 show a second embodiment of the present invention. This embodiment is a deterioration diagnosis method for an electronic circuit board used under atmospheric conditions. The target for diagnosing life span of this embodiment is a conductor of an electronic circuit board, with the conductor being made of the metal copper. As one of the environmental factors is that copper is particularly susceptible to corrosion by hydrosulfuric gas, in atmospheric conditions where hydrosulfuric gas is dominant, an assessment point per hydrogen sulfide factor is multiplied by a eighting coefficient of greater than one. In other words, coefficients corresponding to hydrogen sulfide are corrected at the weighting factor correction unit 7 of FIG. 1. A corrosion loss function Wcu for copper becomes the following formula (6) from formula (4).

$$Wcu = fcu(E,d) = \alpha cu(E) \cdot \sqrt{d} + \beta cu(E) \quad (6)$$

However, an amount of corroded copper calculated from the formula (6) cannot be directly applied to the amount of corrosion of a conductor.

This is because a conductor of an electronic circuit board is not directly exposed to atmospheric conditions.

As shown in FIG. 9, the solder resist 20 is printed on the surface of the conductor 19.

Numeral 18 is a base material.

Corrosion of the conductor 19 occurs due to corrosive gases, sea salt particles, or water permeating in from a pinhole of the solder resist 20.

In this case, a copper board and a model circuit board are exposed in an environmental test tank, and a function such as FIG. 10A is created beforehand by studying the relationship between an amount of corrosion of a copper plate and thickness of corrosion of the conductor of the electronic circuit board at prescribed periods of time. This function is stored at the life span factor conversion database 16 of FIG. 1.

Various functions obtained from environmental tests performed by changing combinations of conditions such as temperature, humidity, types and density of corrosive gas are then stored.

In a cross-sectional view of corrosion of a conductor of an electronic circuit board shown in FIG. 11, corrosion of a corroding part 19a is progressing in a localized manner, and thickness of corrosion is measured at the portion of the corroding part 19a where corrosion has progressed the most.

From equation (6), corroded amount of copper can be predicted after t hours since the copper is set under a relating atmospheric environment, and therefore, due to the relative curve of FIG. 10A, thickness of corrosion of a conductor after t hours corresponding to the corroded amount of the copper after t hours can be estimated. As a result, it is possible to judge a deterioration condition of corrosion of the conductor.

Life span prediction is performed using the following method.

The thickness of corrosion of a conductor compared to the initial thickness of the conductor is referred to as a corrosion loss rate.

Because corrosion of a conductor progresses rapidly when the thickness of the conductor becomes less then half of the initial thickness, a corrosion loss rate of 40% to 50% is taken as a life span limit determining value.

As corrosion of a fine wire pattern of a conductor width of 250 μm or less progresses quickly once corrosion starts, a limit for the corrosion loss rate is taken to be 40%. When the conductor width is greater than 250 μm, the limit for the corrosion loss rate is taken to be 50%.

For example, the corrosion limit thickness of a conductor 150 μms wide and 35 μms thick is 35×0.4=14 μm. The limit for an amount of corrosion of copper corresponding to conductor corrosion limit thickness is obtained in the manner shown in FIG. 10B.

Next, from the limit of the amount of corrosion of the copper, the time taken to reach the limit for the amount of corrosion of the copper is obtained using the formula (5). This is the time for the life span of the conductor of the electronic circuit board under atmospheric conditions.

The selected target for the conductor to be diagnosed is taken to be the most narrowest width of the electronic circuit board. In order to increase the precision of life span prediction, a method for correcting the relationship between corrosion loss and time after a copper board is exposed to atmospheric conditions over a period of time and the amount of corrosion is measured, and a method for correcting the function of FIG. 10A by measuring a product board or the thickness of the corrosion of a board conductor for life span diagnosis during a periodical inspection can be used.

In addition, there are boards where not only solder resist, but also coating agent for improving environmental resistance is applied on the surface of the conductor of the electronic circuit board, or non-washed boards left with solder flux used during the parts mounted process.

Therefore, a function for the thickness of corrosion of a conductor and a corroded amount of copper as shown in FIG. 10A is made for each kind of board and stored at the life span factor conversion database 16.

FIG. 12 to FIG. 16 show a third embodiment of the present invention.

Figure 12:
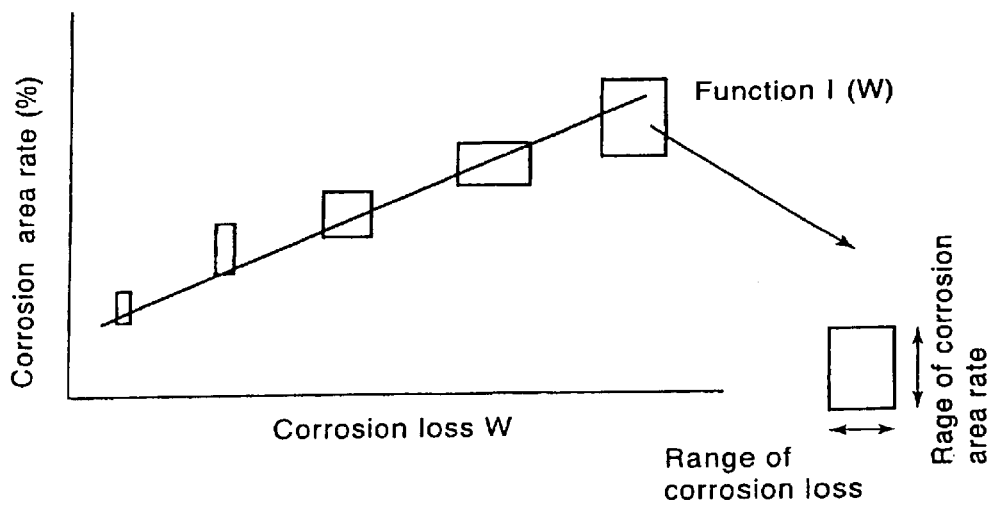
FIG. 12 is a graph showing the relationship between the corrosion loss of aluminium and the corroded area percentage of the aluminium wiring of an integrated circuit in a third embodiment of the present invention.
Figure 15:
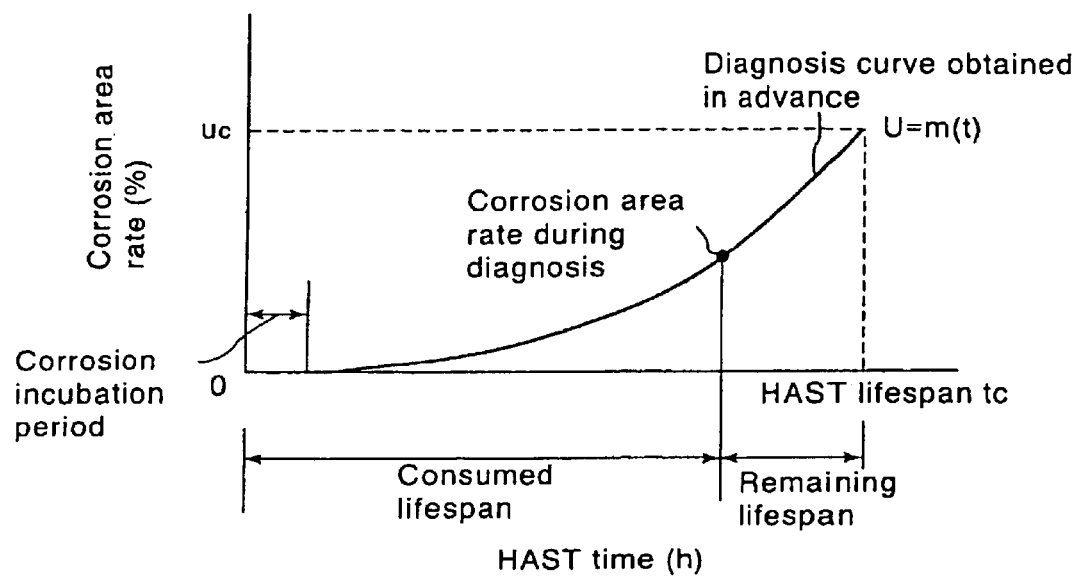
FIG. 15 is a graph to illustrate the detail of the time series curve U=m(t) for the aluminium wiring corroded area percentage of an integrated circuit in the above third embodiment.
Figure 16:
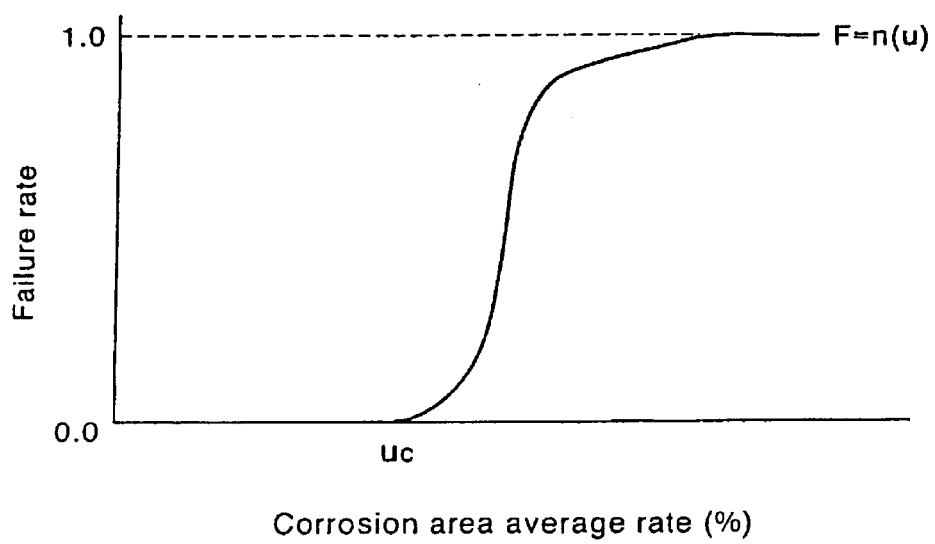
FIG. 16 is a graph to illustrate the detail of the aluminium wiring corroded area percentage and the correlation curve for damage F=n(U) in the above third embodiment.

FIG. 12 is a drawing showing a correctional function 1(W) between corrosion loss of aluminum and a corroded area rate of aluminum wiring of an integrated circuit obtained using an accelerated deterioration test, FIG. 13 is a drawing describing details of a corroded area rate database stored at the life span factor conversion database 16 of FIG. 1, FIG. 14 is a drawing describing details of a life span diagnosis database also stored at the life span factor conversion database 16 of FIG. 1, FIG. 15 is a drawing describing details of a time serial curve U=m(t) of a corroded area rate of aluminum wiring of an integrated circuit, and FIG. 16 is a drawing describing details of a correctional curve F=n(U) between a corroded area ratio of aluminum wiring and a failure.

First, as described in the first embodiment, an environmental factor amount is measured, and corrosion loss of aluminum under the atmospheric conditions Wa1=f(E, d) is calculated.

Next, the operation results are substituted in the correctional function U=l(W) for the aluminum corrosion loss Wal and the corrosion area rate of aluminum wiring of an integrated circuit prepared beforehand at the life span factor conversion database 16, and the corrosion area rate of the integrated circuit is derived.

When the time series change curve U=m(t) of the corrosion area rate of aluminum wiring of an integrated circuit is created, the correctional function l(W) is created by performing an accelerated deterioration test on an aluminum test piece under the same conditions.

At desired times, samples are taken from a plurality of integrated circuits and a plurality of testpiece evaluation tanks, and the corrosion area rate of the aluminum wiring of the integrated circuits and corrosion loss of the aluminum test pieces is measured. Data is then plotted along both axes of the graph with a certain distribution width, as shown in FIG. 12.

During this time, a correlative curve is derived by subjecting data for the average values of each distribution to regression approximation.

A corrosion area rate for aluminum wiring of an integrated circuit can be derived as the correlative curve, by substituting the results of the operation for the corrosion speed dWal/dt=g(E,d) under atmospheric conditions using a correlative function for the aluminum corrosion speed dWal/dt and the corrosion area rate of the aluminum wiring of the integrated circuit.

The trend of the correlative curve U=l(W) or U=l(dW/dt) is known to vary depending on, for example, the material of an integrated circuit and type of a circuit.

Therefore, with regards to types of integrated circuits used for judging a condition of corrosion deterioration, it is necessary to create a correlative curve U=l(W) or U=l(dW/dt) for every type of circuit in advance and to store these curves in a database, as shown in FIG. 13.

Next, the derived corroded area rate of the integrated circuit is verified with the life span diagnosing database. A time serial curve U=m(t) of corrosion area rate of aluminum wiring corresponding to materials of integrated circuit, types of circuit, and dates, and a correlation function F=n(U) for the corrosion area rate of aluminum wiring and failure rate are stored at the life span diagnosing database, as shown in FIG. 14.

Therefore, U=m(t) and F=n(U) of a designated object can be retrieved. U=m(t) and F=n(U) generally show trends such as shown in FIG. 15 and FIG. 16 respectively, and the curve rate and the absolute value are slightly different depending on the materials of the integrated circuit, types of circuits and dates, etc.

However, a life span point (a point where the failure rate drastically increases toward the corrosion area rate) of the integrated circuit can be defined from a relative curve F=n(U) between corrosion area rate and failure rate. This point is taken to be a life span point corrosion quantity uc, and life span can be estimated by setting a life span time tc satisfying $tc=m^{-1}(uc)$ on the time series curve for corrosion area rate.

In other words, when T is a time derived from the relationship between the corrosion area rate of the integrated circuit derived from a series of procedures of the environmental factor measurement during diagnosis and U=m(t) of FIG. 15, the time T is equivalent to the consumed life span of FIG. 15 and equivalent to the usage time on the real time axis.

On the other hand, because life span is obtained by tc-T on the time axis during an acceleration test, life span on the real time axis can be calculated using proportional distribution formula (life span)=(usage time)×(tc-T)/T. After diagnosed results are output to a CRT and a printer, etc. using the diagnosis results display unit 15 as well as being output to a recording medium so that results can be put into the database, the results are used when life span of the same type of equipments and integrated circuits is diagnosed. As above, in the life span diagnosis method of the embodiment, by preparing in advance a correlation function between a corrosion area rate of aluminum wiring of an integrated circuit and a corrosion loss (or corrosion speed) of aluminum, it is possible to estimate life span of non-failing integrated circuits by measuring quantities of environmental factors for an installed equipment without measuring an actual quantity of corrosion for aluminum wiring by opening the integrated circuit.

Figure 17:
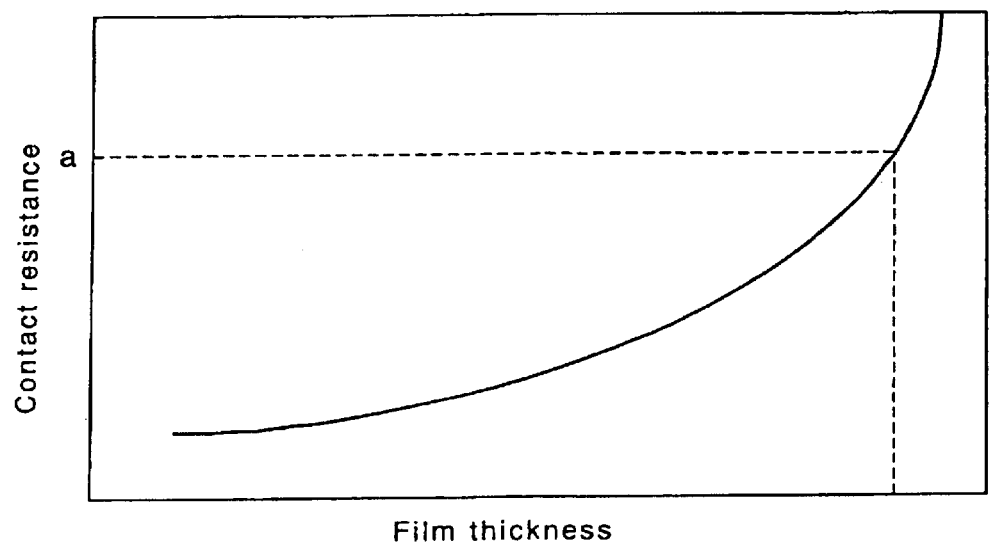
FIG. 17 is a graph showing the relationship between corrosion film thickness and contact resistance in a fourth embodiment of the present invention.
Figure 18:
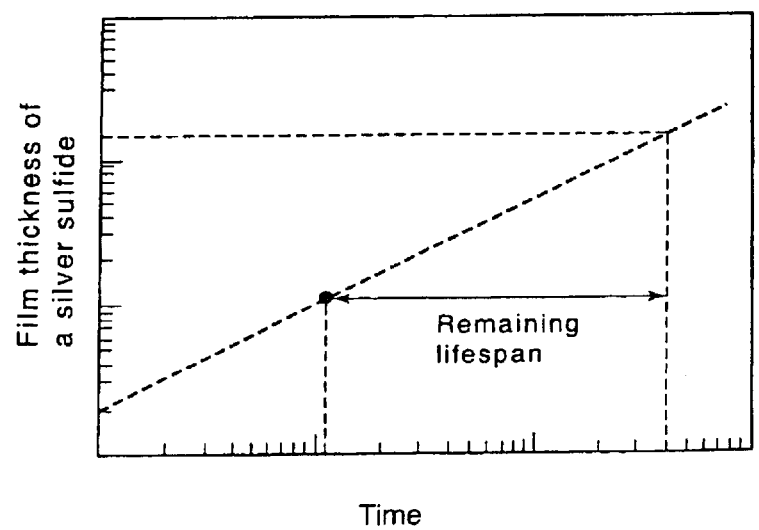
FIG. 18 is a drawing showing the relationship between film thickness of silver sulfide and exposure time in the above fourth embodiment.

FIG. 17 and FIG. 18 show a fourth embodiment of the present invention.

The target for diagnosing life span of this embodiment is a part having a metal contact point such as a relay used in an electronic circuit, and main metal causing deterioration of the functioning of the part is made of silver.

As stated in the first embodiment, environmental factor quantities are measured, and a corrosion function for silver is obtained.

At the silver metal contact point, because functional deterioration is caused by the thickness of a silver sulfide corrosion film, a silver plate is exposed in an environmental test tank as in the second embodiment, a functional relation is obtained by studying the relationship between an amount of corrosion of a silver plate and the thickness of a corrosion film of silver sulfide at prescribed periods of time.

This function is stored in the life span factor conversion database 16 of FIG. 1, where types of functions obtained from environmental tests performed by changing combinations of conditions such as temperature, humidity, types and density of corrosive gas are stored.

The function is then converted to the thickness of corrosion film of silver sulfide using the corrosion material function of silver obtained from the metal corrosion function generation unit 8, using a function stored at the life span factor conversion database 16. An existing contact resistance is obtained from the relationship between the film thickness and the contact resistance shown in FIG. 17, and a condition of corrosion deterioration of a silver contact point is determined. Also, as shown by "a" in FIG. 17, a limit value for increasing the contact resistance of a silver contact point of the electronic circuit is set, and as shown in FIG. 18, by predicting corrosion loss in the environment using the above calculation, corrosion film growth is predicted, the time taken to reach a corrosion film thickness corresponding to the limit value of contact resistance is calculated, and life span of the contact point of the silver used in the environment is determined.

The limit value for increasing contact resistance of the silver contact point shown by "a" in FIG. 17 is also stored at the life span factor conversion database 16, and the life span shown in FIG. 18 is calculated at the part life span calculation unit 17.

Therefore, using above method, it is possible to determine the deterioration condition of a silver contact point comprising an electronic circuit used under atmospheric conditions without stopping an equipment, and to predict life span of a silver contact point in the environment.

Figure 19:
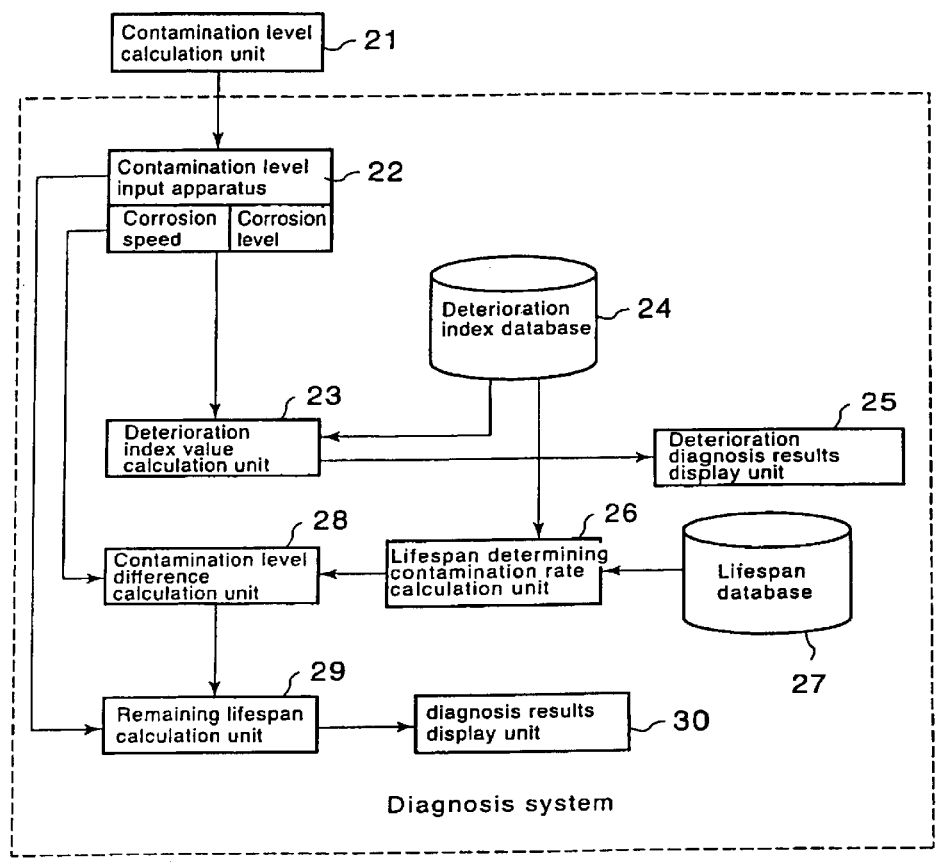
FIG. 19 is a block diagram of corrosion diagnostic equipment that is a fifth embodiment of the present invention.

FIG. 19 shows a fifth embodiment of the present invention.

In FIG. 19, numeral 21 indicates contamination speed measuring means for measuring contamination speed.

A contaminated substance on the surface of an electronic circuit is sampled from a set area and dissolved in a set amount of pure water. The electric conductivity of the contaminated solution is then measured.

The correlation relationship between concentration and electric conductivity of a water solution of sodium chloride is obtained beforehand, and the electric conductivity of the contaminated solution is converted to a concentration of sodium chloride using this relationship.

Using the converted concentration of sodium chloride, volume of the contaminated solution, and the sample area of the contaminated substance, an equivalent amount of salt of the contaminated substance adhered to per unit area of the electronic circuit board, in other words, a contamination speed, is obtained.

The contamination speed is obtained by dividing the contamination speed by the time passed since the installment of the electronic circuit board.

Also, as conditions of use of electrical equipment can sometimes differ between the initial delivered time and the diagnosis time, in order to precisely obtain the current contamination speed, it is desirable that a second contamination speed measurement is performed after a certain period of time has passed since the initial measurement, and then the contamination speed from the increased contamination is obtained.

If it is difficult to measure the product electronic circuit board twice, there is another method of obtaining the contamination speed using the measuring results of contamination speed of a board after the board for measuring contamination speed is exposed in the control board for certain period of time.

Instead of the above contamination speed, it is also possible to use a method for obtaining a total adhered amount of chlorine ions, nitrate ions, and sulfate ions that become adhered on the surface of the electronic circuit board per unit area.

More precise diagnosis is also possible by using the total amount of the three types of negative ions deposited having the most substantial influence on insulation drops and corrosion in place of the contamination level.

Negative ion measurements can easily be obtained by analyzing the contaminant used in the contamination level (pollution level) measurements.

Contamination levels and contamination speeds measured at the contamination speed measuring means (unit) 21 are sent to the deterioration index value calculation unit 23 as means (unit) for calculating deterioration index values inputted by the contamination level input apparatus 22. The deterioration index value calculation unit 23 reads correlation functions for the corrosion rate and deterioration index stored in the deterioration index database 24 and calculates deterioration index values corresponding to the inputted contamination rate.

A deterioration index for a correlation function stored in the deterioration index database 24 consists of a vibration rate of fractal dimension for the heat distribution image for the electronic circuit board, wire-breaking time due to corrosion of the conductor pattern of the electronic circuit board and insulation resistance values between conductors of the electronic circuit board.

Deterioration index values calculated at the deterioration index value calculation unit 23 show the characteristic values of the deterioration index at the time of diagnosis and are therefore displayed at a deterioration diagnosis results display unit 25 as deterioration diagnosis results.

Next, life span diagnosis is carried out.

Life span threshold values are read from a life span database 27 storing life span threshold values for each type of deterioration index of the electronic circuit boards and the life span threshold values are sent to a life span-determining contamination rate calculation unit 26.

The life span threshold values are then substituted into a correlation function for the contamination rate the deterioration values stored in the deterioration index database 24 and the life span-determining contamination rate is calculated and sent to a contamination level difference calculation unit 28 as means (unit) for calculating the difference in contamination rates.

At the contamination level difference calculation unit 28, differences between contamination levels sent from the contamination level input apparatus 22 and the life span-determining contamination levels sent from the life span-determining contamination level calculation unit 26 and are sent to a remaining life span calculation unit 29 as means for calculating the remaining life span.

At the remaining life span calculation unit 29, differences in the levels of contamination sent from the contamination level difference calculation unit 28 are divided by the contamination speeds sent from the contamination level input apparatus 22 and the remaining life span is calculated. The results of the calculations are then displayed at an evaluation results display unit 30.

According to this embodiment, as a result of preparing a correlation function for the contamination level (pollution level) and the insulation deterioration or deterioration index for the electronic circuit board relating to corrosion, life span (life duration) of an electronic circuit board can be estimated just by measuring contamination levels without having to make electrodes for carrying out measurements on the board or damaging the board by performing deterioration measurements.

Figure 20:
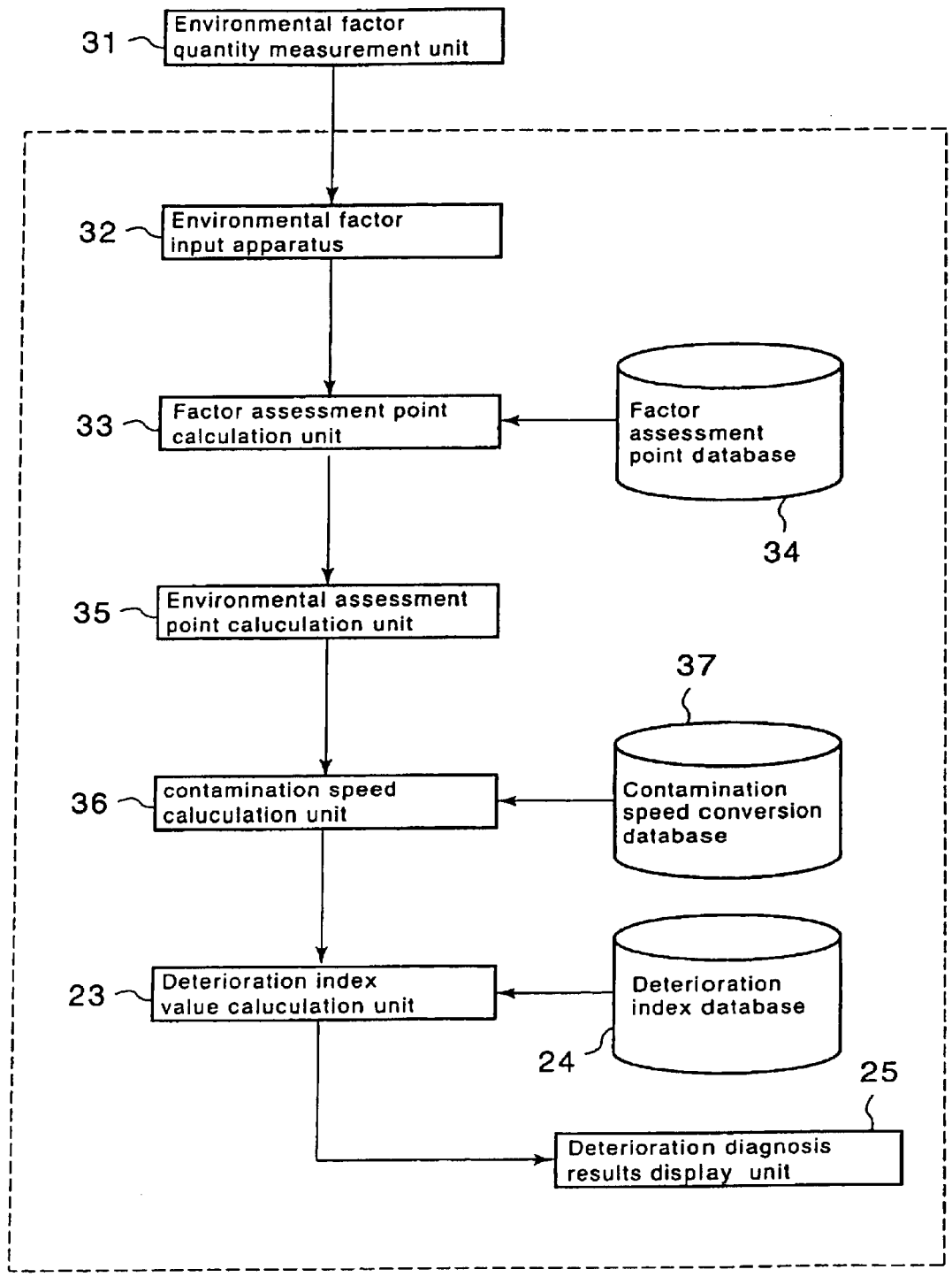
FIG. 20 is a block diagram of environmental assessment point-based corrosion diagnostic equipment that is a sixth embodiment of the present invention.

FIG. 20 shows a sixth embodiment of the present invention.

In this embodiment, there is a correlation function for the environmental evaluation points numerically representing the whole of the influence of the adhesion and bringing in of floating dust within the atmosphere and the influence of amounts of corrosive gas and sea salt particles within the atmosphere and the contamination levels, with the environmental assessment points then being employed in place of the contamination levels as the index for environmental contamination.

FIG. 20 shows the configuration of this embodiment.

In FIG. 20, numeral 31 represents environmental factor measuring means (unit) for measuring atmospheric conditions, comprising a corrosive gas densitometer, a thermometer, a relative humidity meter, and sea salt particle measuring means, etc.

Each of the measuring means (unit) are installed in an environment so as to measure the atmospheric conditions for a period of one to two months.

Quantities for each of the environmental factors measured at the environmental factor measuring means (unit) 31 are sent to a factor assessment point calculation unit 33 by an environmental factor input apparatus 32.

The factor assessment point calculation unit 33 reads data showing the relationship between factor quantities and factor quantity assessment points, provided by a factor assessment point database 34 employing an output of the environmental factor input apparatus 32, and calculates factor assessment points.

The sum of each of the factor assessment points calculated at the factor assessment point calculation unit 33 is calculated at an environment assessment point calculation unit 35.

The contamination speed is then calculated at a contamination speed calculation unit 36 by substituting environment assessment points calculated at the environment assessment point calculation unit 35 and contamination speeds in the correlation function for the environment assessment points stored in a contamination speed conversion database 37. An estimated contamination speed during diagnosis is then obtained by multiplying the calculated contamination speed by the number of years of usage in the environment.

The contamination speed calculated at the contamination speed calculation unit 36 is sent to the deterioration index value calculation unit 23. This contamination speed is then substituted into the correlation function for the contamination level stored in the deterioration index database 24 and the characteristic values for the deterioration index at the time of diagnosis are calculated, and the diagnosis results are displayed at the deterioration diagnosis results display unit 25.

Contamination speeds and contamination levels are converted from the environmental assessment points and life span diagnosis can be carried out in the same manner as for the fifth embodiment.

According to this embodiment, environmental assessment points are obtained in place of contamination level measurements in cases where measuring of contamination levels of an electronic circuit board located behind a control panel etc. is difficult or where a board is operating continuously and cannot be stopped. It is then possible to subject an electronic circuit board to life span diagnosis using contamination levels converted from the environmental assessment points.

Figure 21:
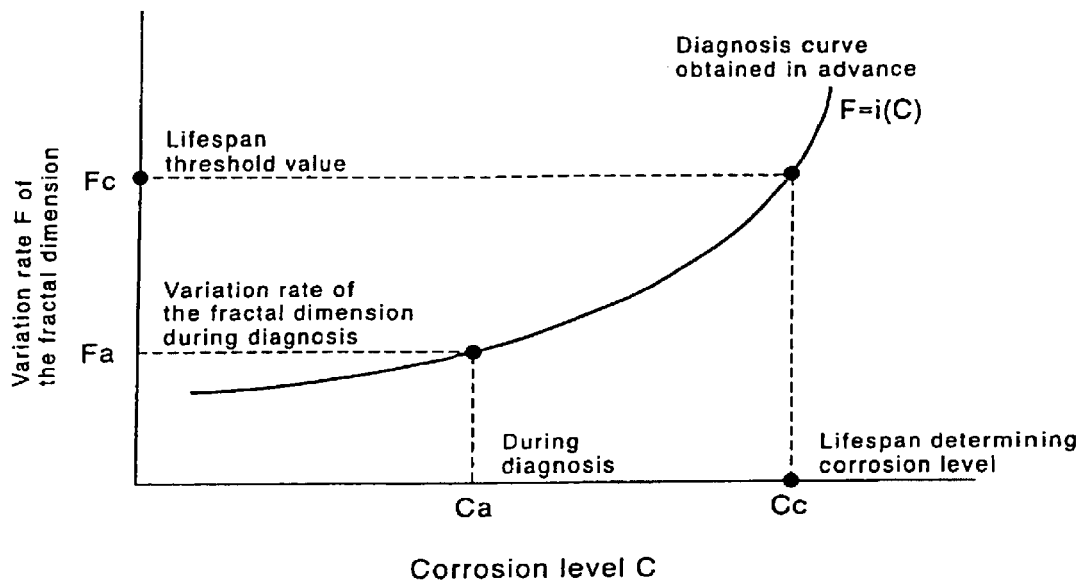
FIG. 21 is a graph showing the relationship between degree of soiling and percentage fractal dimensional variation (variation rate of fractal dimension) in a seventh embodiment of the present invention.
Figure 22:
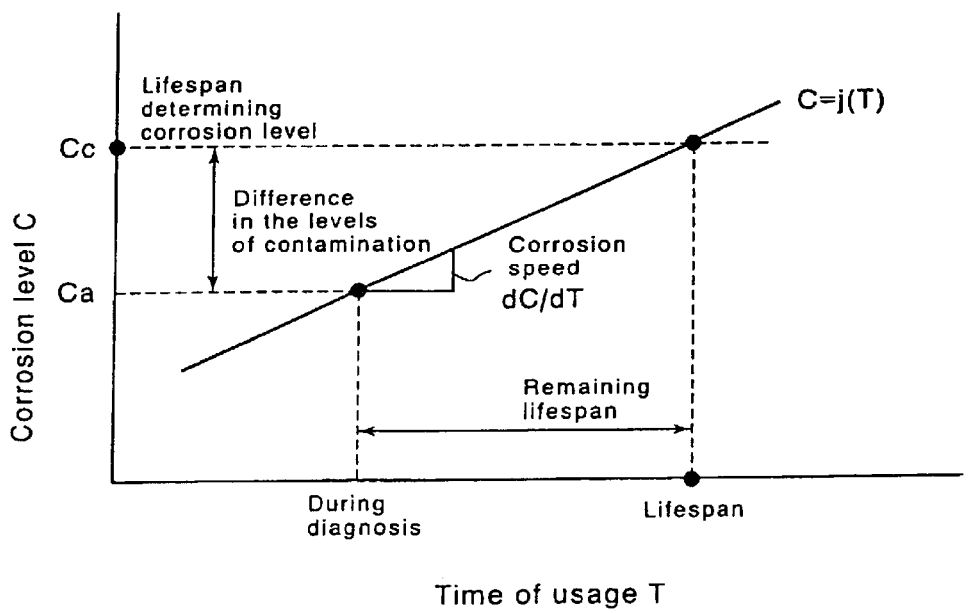
FIG. 22 is a drawing showing the variation with passage of time of the degree of soiling in the above seventh embodiment.

FIG. 21 and FIG. 22 show a seventh embodiment of the present invention.

FIG. 21 is a view illustrating the correlation function for a contamination level C of the surface of the electronic circuit board and a variation rate of fractal dimension F stored in the deterioration index database 24.

Figure 25:
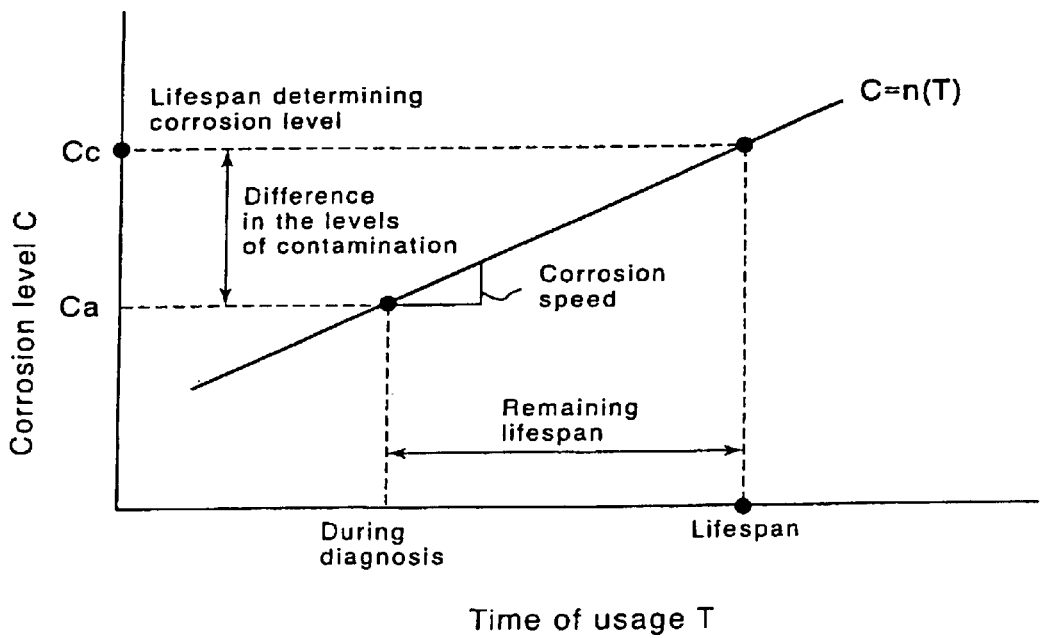
FIG. 25 is a drawing showing variation with passage of time of the degree of soiling in the above ninth embodiment.

FIG. 25 is a view showing deterioration with age of the contamination level C of the environment. First of all, contamination level and contamination speed are measured as shown in the fifth embodiment or the sixth embodiment.

Next, the obtained contamination level Ca is substituted in the correlation function $F=i(C)$ for the contamination level C and the variation rate of fractal dimension F stored in advance in the deterioration index database 24, variation rate of fractal dimension Fa of the fractal dimension during diagnosis is obtained, and the state of deterioration during diagnosis is diagnosed.

The correlation function $F=i(C)$ is obtained in advance by field salvage and environmental deterioration testing.

The variation rate of fractal dimension is obtained by calculating a fractal dimension for heat distribution images for the whole board collected periodically from the start of conduction at the electronic circuit board, with the rate of change being calculated for each period. Correlation functions for the contamination rate and the variation rate of fractal dimension depending on the types of parts mounted on the electronic circuit board and the interconnect state of the conducting pattern and must therefore be stored in advance in the deterioration index database 24 for each type of electronic circuit board.

Next, a life span threshold value Fc for the variation rate of fractal dimension of the substrate to be diagnosed is called from the life span database 27.

Life span threshold values are obtained in advance for every type of electronic circuit board from the relationship between the variation rate of fractal dimension and the failure rate.

This life span threshold value is substituted into the correlation function $F=i(C)$ for a corrosion level C and variation rate of fractal dimension F stored in the deterioration index database 24, and a corrosion level equivalent to the life span threshold value Fc, namely the life span deterring corrosion level Cc, is calculated.

FIG. 22 is a drawing showing a function $C=j(T)$ of deterioration with age of the contamination level C for certain environments.

A time from the corrosion level at the time of diagnosis until the life span-determining corrosion level is reached, namely the remaining life span, can be estimated by dividing a difference corrosion level obtained by subtracting the corrosion level Ca at the time of diagnosis from the life span-determining corrosion level Cc by the corrosion speed for the particular environment $dC/dT$, that is to say, the estimated remaining life span=$(Cc-Ca)/(dC/dT)$.

Figure 23:
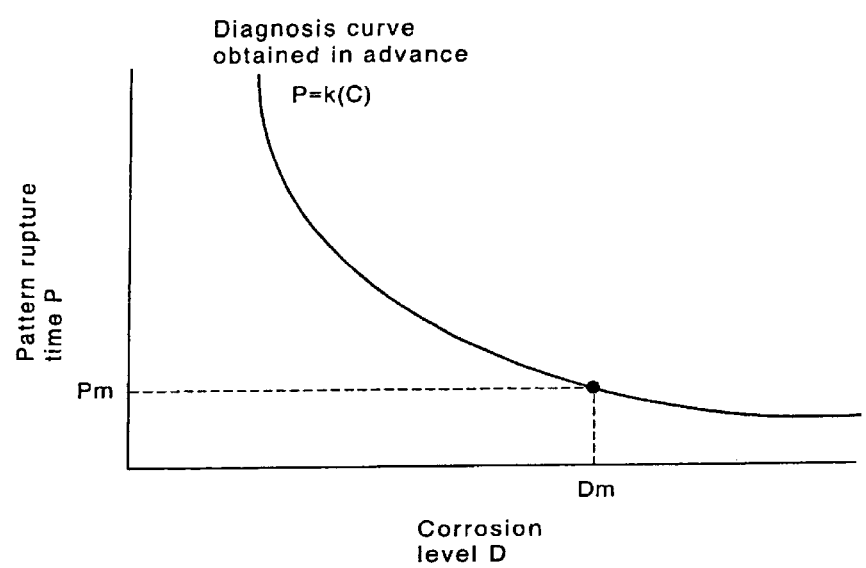
FIG. 23 is a graph showing the relationship between soiling rate and conductor pattern corrosion breakage time in an eighth embodiment of the present invention.

As described above, according to the present embodiment, by obtaining a correlation function for the variation rate of fractal dimension and contamination level for the electronic circuit substrate and without taking the substrate out from a control panel for measurement or attaching electrodes for insulation value measurement, it is possible to estimate the life span of an electronic circuit substrate based on the variation rate of fractal dimension by simply obtaining a total sticking amount of negative ions (chlorine ions, nitrate ions, sulfate ions) or environmental assessment points, instead of bringing about new conductance or having to provide special apparatus for carrying out measurements FIG. 23 shows an eighth embodiment of the present invention. FIG. 23 is a view illustrating the correlation function for a contamination level D of the surface of the electronic circuit board and a time P until a conducting pattern of an electronic circuit board breaks stored in the deterioration index database 24.

First of all, corrosion speed is measured as shown in the fifth embodiment and the sixth embodiment.

Next, the obtained corrosion speed Dm is substituted into the correlation function $P=k(C)$ of FIG. 23 stored in advance in the deterioration index database 24 for the corrosion speed D and the pattern rupture time P, and the time Pm to pattern rupture is calculated.

The obtained pattern rupture time Pm represents a time from installation in an appropriate environment to conductive pattern rupture.

The correlation function $P=k(C)$ is previously obtained by field salvage and environmental degradation testing.

Since the tendency of the correlation function $P=k(C)$ for corrosion speed D and the pattern rupture time P is different depending on pattern width, pattern metal thickness, and pattern surface solder resist film thickness etc., it is necessary to store a separate correlation curves for pattern structures of electronic circuit substrates to be diagnosed in the deterioration index database 24.

Obviously, wiring patterns of various thicknesses are arranged on the electronic circuit substrate, but life span determination for the electronic circuit substrate concerned is carried out for the thinnest pattern.

As described above, according to the present embodiment, simply by obtaining a relationship between conductive pattern rupture time and corrosion speed for the electronic circuit substrate and without destroying a product substrate and examining a corroded condition of a pattern, by simply obtaining a corrosion speed, sticking rate of negative ions (chlorine ions, nitrate ions, sulfate ions) instead of the corrosion level or environmental evaluation points it is possible to estimate life span until the pattern ruptures.

Figure 24:
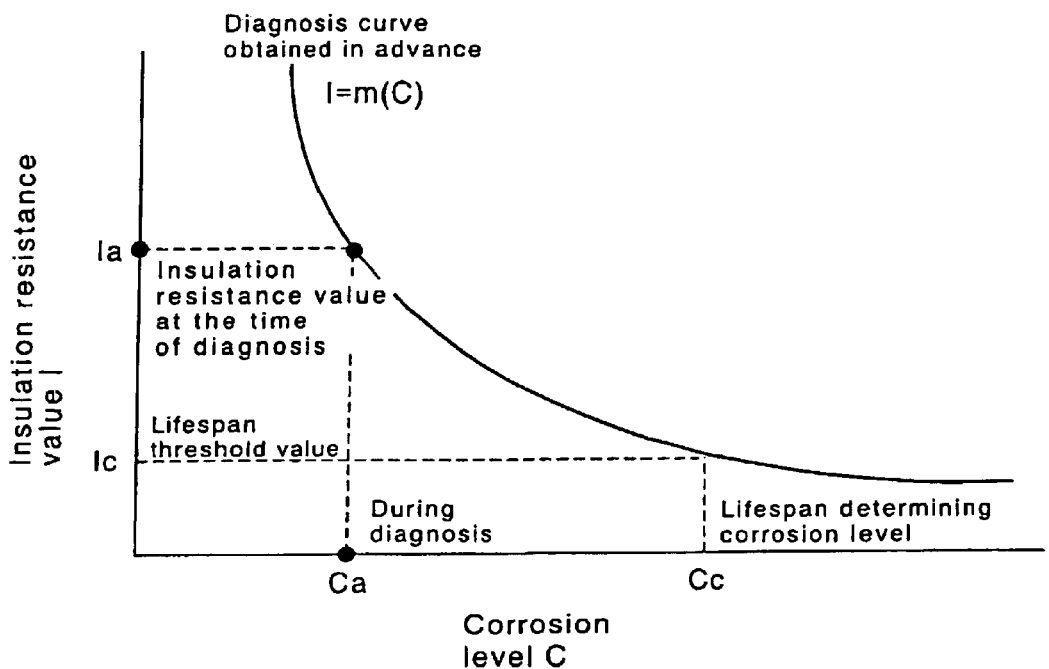
FIG. 24 is a graph showing the relationship between degree of soiling and inter-conductor insulation resistance value of an electronic circuit board surface in a ninth embodiment of the present invention.

FIG. 24 and FIG. 25 show the ninth embodiment of the present invention.

FIG. 24 is a drawing for describing a correlation function for a corrosion level C of an electronic circuit substrate surface and an insulation resistance value I between conductors, stored in the deterioration index database 24.

FIG. 25 is a drawing showing deterioration with age of the corrosion level C or certain environments. First of all, contamination level and contamination speed are measured as shown in the fifth embodiment or the sixth embodiment.

Next, the obtained corrosion level Ca is substituted into the correlation function I=m(C) of FIG. 23 for corrosion level C and insulation resistance value I stored in advance in the deterioration index database 24, an insulation resistance value Ia at the time of diagnosis is obtained and degradation condition at the tem of diagnosis is diagnosed.

The correlation function I=m(C) is previously obtained by field salvage and environmental degradation testing.

Next, a life span threshold value Ic for the insulation resistance of the substrate to be diagnosed is called from the life span database 27.

The life span threshold value is set for every type and specification of electronic circuit substrate, based on places where it is most susceptible to the effects of insulation lowering.

This life span threshold value is substituted into the correlation function I=m(C) for corrosion level C and insulation resistance value I stored in the deterioration index database 24, and a corrosion level equivalent to the life span threshold value Ic, namely the life span-determining corrosion level Cc, is calculated.

FIG. 25 is a drawing showing a function C=n(T) of deterioration with age of the corrosion level C for certain environments.

A time from the corrosion level at the time of diagnosis until the life span-determining corrosion level is reached, namely the remaining life span, can be estimated by dividing a difference corrosion level obtained by subtracting the corrosion level Ca at the time of diagnosis from the life span-determining corrosion level Cc by the corrosion speed for the particular environment dC/dT, that is to say, the estimated remaining life span=(Cc−Ca)/(dC/dT).

As described above, according to the present embodiment, by obtaining a correlation function for insulation resistance value and corrosion level for the electronic circuit substrate and without taking the substrate out from a control panel for measurement or attaching electrodes for insulation value measurement, it is possible to estimate the life span of the electronic circuit substrate due to insulation breakdown by simply obtaining a total sticking amount of negative ions (chlorine ions, nitrate ions, sulfate ions) or environmental evaluation points, instead of the corrosion level or corrosion speed.

Also, according to this embodiment, it is easy for insulation breakdown to occur due to environmental pollution, but insulation breakdown conditions between components leads chat can not be measured, for example, can be estimated from the corrosion level.

Also, the technique described in the present invention can be distributed as a program executed on a computer, using a medium, or by transmission using a LAN or the Internet.

As a storage medium, magnetic disc, floppy disc, a hard disk, optical disk or magneto-optical disk can be used, and in fact any type of medium is acceptable as long as it can be read by a computer.

As described above, according to the deterioration diagnosis method of the present invention, the corrosion loss of the metallic material in the atmosphere for the exposure days is formulated as a function for environmental evaluating points which represents the level of the harmfulness of the atmospheric conditions, and the life span of the metallic material is diagnosed based on the corrosion loss obtained from the function, which means that the amount of corrosion loss of the metallic material under atmospheric conditions can be calculated by the measurement and the evaluation of the environmental evaluation points of the atmospheric environment without the long-term atmospheric exposure test of the metallic material, and the life span of the metallic material can be diagnosed for the atmospheric conditions.

Additionally, according to the deterioration diagnosis method of the present invention, since a corrosion speed of a metallic material under atmospheric conditions is formulated as a function for environmental assessment points which represents a level of harmfulness of the atmospheric conditions, and a life span of the metallic material is diagnosed based on the corrosion speed calculated from the function, the amount of corrosion loss of the metallic material under atmospheric conditions can be calculated by the measurement and the evaluation of the environmental evaluation points of the atmospheric environment without the long-term atmospheric exposure test of the metallic material, and the life span of the metallic material can be diagnosed for the atmospheric conditions.

Additionally, according to the deterioration diagnosis method of the present invention, since assessment points and a weighting factor for each factor are assigned according to the amount of each of the plurality of environmental factors, including temperature, humidity, corrosive gas, sea salt particles in the atmospheric environment or the distance from the coast, and the environmental evaluation points are the sum of the products of the assessment points and the weighting factor of each factor, environmental assessment points for calculation of corrosion loss and corrosion speed can be appropriately obtained Additionally, according to the deterioration diagnosis method of the present invention, since the assessment points for each of the plurality of environmental factors, including temperature, humidity, corrosive gas, sea salt particles in the atmospheric environment or the distance from the coast, are assigned after classification according to the range of the amount of each environmental factor, or are the function of a median of the amount of each environmental factor, factor assessment points for establishing environmental assessment points can be appropriately determined.

Additionally, according to the deterioration diagnosis method of the present invention, since a method for measuring a corrosive gas amount for an environmental factor is a filter paper method, in which an amount of gas absorbed on a filter exposed for a prescribed period under atmospheric conditions is obtained, a method of measuring acid gas in the corrosive gas, using an alkaline filter paper, which is made of cellulose and impregnated with either of a potassium carbonate solution of a prescribed % or a sodium carbonate solution of a prescribed %, and a method of measuring an amount of alkaline gas in the corrosive gas, using an acid filter paper which is made of glass and impregnated a phosphoric acid solution of a prescribed %, are performed, it is possible to perform measurements taking atmospheric conditions such as wind speed and wind amount into consideration by adopting a filter paper method in the corrosive gas amount measurement, and since the filter paper can be exposed close to the object of diagnosis using a small piece of paper it is possible to accurately measure the environment bleached by the subject of diagnosis. Accordingly, it is possible to perform precise diagnosis of metallic material life span.

Still further, according to the deterioration diagnosis method of the present invention, since the assessment points for each factor assigned according to a range of amount of each environmental factor are divided into at least 5 classes it is possible to more subtly partition actual environments by dividing into five classes in a range of actually existing measurement values, and it is possible to precisely determine environmental conditions.

Accordingly, it is possible to perform more precise diagnosis of metallic material life span.

Additionally, according to the deterioration diagnosis method of the present invention, since the assessment points for the relative humidity under atmospheric conditions where the object is exposed directly to rain and snow are calculated as the sum of the assessment points in each class and the prescribed compensation points, in the case of direct contact with outdoor atmospheric conditions such as rain or snow, and since the effect of promoting corrosion is substantial, it is possible to appropriately determine an assessment point for humidity in order to precisely diagnose corrosiveness of the atmospheric conditions.

Additionally, according to the deterioration diagnosis method of the present invention, since assessment points for sea salt particles as an environmental factor are assigned according to the classification by the distance from the coast, which means that the basis for classification and factor assessment points is distance from the coast at a few hundred locations around the country having different governing environmental factors, sea salt particle measurement values, and investigation results for corrosiveness of metal material exposed to these environments.

As a result, it is possible to obtain assessment points for a sea salt particles environmental factor by simply obtaining a distance from the coast on a map, without actually measuring the amount of sea salt particles.

Additionally, according to the deterioration diagnosis method of the present invention, since a specified metallic material is exposed under the atmospheric conditions for a prescribed period, and the amount of weight loss due to corrosion is measured for the number of exposure days of the prescribed period, and the environmental assessment points are calculated by the amount of the corrosion loss and the number of exposure days, and the life span of another metallic material is diagnosed using these environmental assessment points, the life span of any other metallic material can be diagnosed by the reverse calculation of the environmental assessment points from the number of exposure days and amount of corrosion loss of the specified metallic material, without the need for a long-term atmospheric exposure test of the metallic material.

Additionally, according to the deterioration diagnosis method of the present invention, copper is used as the specific metallic material, and copper is highly sensitive against corrosion under atmospheric conditions, including all environmental factors, and therefore the environmental assessment points can be determined by the inverse calculation with high accuracy.

Additionally, according to the deterioration diagnosis method of the present invention, the amount of corrosion loss of the metallic material under atmospheric conditions is represented by the linear expression of the square root of the number of exposure days of the metallic material under atmospheric conditions. Also, the functions in the linear expression are represented by the polynomial expression of the environmental assessment points.

Therefore the relationship between the number of exposure days of the metallic material under atmospheric conditions and the amount of corrosion loss can be obtained by the measurement and the evaluation of the environmental assessment points of the atmospheric environment without the long-term atmospheric exposure test of the metallic material, and the life span of the metallic material can be diagnosed.

Additionally, according to the deterioration diagnosis method of the present invention, the amount of corrosion speed of the metallic material under atmospheric conditions is represented by the linear expression of the square root of the number of exposure days of the metallic material under atmospheric conditions, and the functions in the linear expression are represented by the polynomial expression of the environmental assessment points.

Therefore the corrosion speed of the metallic material under atmospheric conditions can be obtained by the measurement and evaluation of the environmental assessment points of the atmospheric conditions and the life span of the metallic material can be diagnosed.

Additionally, according to the deterioration diagnosis method of the present invention, for the atmospheric conditions where the metallic material is used, the plurality of environmental factors, including temperature, humidity, corrosive gas, sea salt particles under atmospheric conditions, or the distance from the coast, are measured for the prescribed period, and the assessment points for each factor are determined according to each measured value, the environmental assessment points are determined according to the assessment points for each factor, and the relationship between the amount of corrosion loss of the metallic material and the number of exposure days is determined according to the determined environmental assessment points.

Therefore the relationship of the number of exposure days of the metallic material under atmospheric conditions and the amount of corrosion loss can be obtained by the measurement and the evaluation of the environmental assessment points of the atmospheric environment without the long-term atmospheric exposure test of the metallic material, and the life span of the metallic material can be diagnosed.

Additionally, according to the deterioration diagnosis method of the present invention, for the atmospheric conditions where the metallic material is used, the environmental assessment points are calculated, and the relationship between the amount of corrosion loss of the metallic material and the number of exposure days is determined according to the calculated environmental assessment points.

Therefore the relationship between the amount of corrosion loss and the number of exposure days of other optional metallic materials can be obtained by the inverse calculation with the single atmospheric exposure rest of the specified metallic material, and the life span of the other optional metallic material can be diagnosed.

Additionally, according to the deterioration diagnosis method of the present invention, for the atmospheric environment where the metallic material is used, the plurality of environmental factors, including temperature, humidity, corrosive gas, sea salt particles under atmospheric conditions or the distance from the coast, are measured for the prescribed period, and the assessment points for each factor are determined according to each measured value, the environmental assessment points are determined according to the assessment points for each factor, and the corrosion speed of the metallic material is determined according to the decided environmental assessment points.

Therefore the corrosion speed of the metallic material under atmospheric conditions can be obtained by the measurement and the evaluation of the environmental assessment points of the atmospheric conditions, and the life span of the metallic material can be diagnosed.

Additionally, according to the deterioration diagnosis method of the present invention, for the atmospheric conditions where the metallic material is used, the environmental assessment points are calculated, and the corrosion speed of the metallic material is determined according to the calculated environmental assessment points.

Therefore the corrosion speed of another optional metallic material can be obtained by the inverse calculation with single atmospheric exposure test of the specified metallic material, and the life span of the other optional metallic material can be diagnosed.

Additionally, according to the deterioration diagnosis method of the present invention, a specified metallic material is exposed under the atmospheric conditions for a prescribed period, the amount of corrosion loss of the metallic material in the prescribed period is measured, and the relationship between the amount of corrosion loss and the number of exposure days is compensated according to the measurement result.

Therefore the relationship between the corrosion loss of the metallic material and the number of exposure days can be compensated to one with higher accuracy, and the life span of the metallic material can be diagnosed with high accuracy.

Additionally, according to the deterioration diagnosis method of the present invention, the metallic material is exposed under the atmospheric conditions for prescribed period, the amount of corrosion loss is measured during the number of exposure days of the prescribed period, and the calculated corrosion speed of the metallic material is compensated according to the measurement result.

The corrosion speed of the metallic material can be corrected to the with higher accuracy by the short-term atmospheric exposure test of the metallic material, and the life span of the metallic material can be diagnosed with high accuracy.

Additionally, according to the deterioration diagnosis apparatus of the present invention, the present invention comprises input means (unit) for inputting the measured value of the amount of each environmental factor measured by measurement means (unit) for the amount of the environmental factors; a first database storing a function which gives a relationship between the amount of each environmental factor and assessment points for each factor; a second database storing a function which gives a relationship between environmental assessment points and the assessment points for each factor for each type of metallic material; assessment points for each factor calculation means (unit) for calculating the assessment points for each factor using a function read out from the first database and an amount of each environmental factor input by the input means (unit); environmental assessment points calculation means (unit) for calculating environmental assessment points which represent a level of the harmfulness of the atmospheric conditions; corrosion loss calculation means (unit) for calculating a relationship between the amount of corrosion loss of the metallic material under the atmospheric conditions and the number of exposure days using a function in which the environmental assessment points calculated by the environmental assessment points calculation means (unit) are formulated as a variable; corrosion speed calculation means (unit) for calculating the corrosion speed of the metallic material under the atmospheric conditions using a function in which the environmental assessment points calculated by the environmental assessment points calculation means (unit) are formulated as a variable; the amount of weight loss due to corrosion correction and calculation means (unit) to correct and calculate the relationship between the amount of weight loss due to corrosion calculated by the amount of weight loss due to corrosion calculation means (unit) based on the amount of weight loss of the metallic material due to corrosion during the exposure days in the prescribed period and the exposure days; corrosion speed correction means (unit) for correcting the corrosion speed calculated by the corrosion speed calculation means (unit) based on the amount of corrosion loss of the metallic material in the number of exposure days of the prescribed period; remaining life span calculation means (unit) for calculating a remaining life span of the metallic material based on the relationship between the corrosion loss corrected by the corrosion loss compensation means (unit) and the number of exposure days, or based on the corrosion speed compensated by the corrosion speed correction means (unit); and output means (unit) for outputting the remaining life span of each metallic material calculated by the remaining life span calculation means (unit) as diagnosis results.

Therefore a series of the necessary processes such as calculation, etc. are carried out just by inputting the measured value of the amount of each environmental factor without the long-term atmospheric exposure test of the metallic material, and the diagnosis result can be outputted with high accuracy.

Additionally, according to the deterioration diagnosis method of the invention in the present Parent Application, with regard to metallic materials that compose electronic circuits, the corrosion loss and corrosion speed are converted to a corrosion deterioration index for a relevant electronic circuit part by applying them to the relationship between a pre-prepared corrosion loss or corrosion speed for the material composing the electronic circuit and the corrosion deterioration indices for electronic circuit parts that are made up of the relevant metallic material, and the corrosion deterioration state of an electronic circuit part is judged by this corrosion deterioration index.

Therefore, the state of deterioration of electronic circuit parts can be judged by measuring and evaluating the environmental assessment points of an atmospheric environment, without the need to withdraw those electronic circuit parts or carry out their destructive testing.

Additionally, according to the deterioration diagnosis method of the invention in the present patent application, when the metallic material composing the electronic circuit is copper and the electronic circuit part is the copper wiring pattern, the corrosion deterioration index is taken as the corrosion thickness of the copper wiring pattern.

Therefore, the state of deterioration of that copper wiring pattern can be judged by measuring and evaluating the environmental assessment points of the atmospheric environment.

Additionally, according to the deterioration diagnosis method of the invention in the present patent application, when the metallic material composing the electronic circuit is aluminium and the electronic circuit part is an integrated circuit, the corrosion deterioration index is taken as the corroded area percentage of the aluminium wiring of the integrated circuit.

Therefore, the state of deterioration of that integrated circuit aluminium wiring can be judged by measuring and evaluating the environmental assessment points of the atmospheric environment.

Additionally, according to the deterioration diagnosis method of the invention in the present Patent Application, when the metallic material composing the electronic circuit is silver and the electronic circuit part is a silver contact, the corrosion deterioration index is taken as the contact resistance value of the silver contact.

Therefore, the state of deterioration of that silver contact can be judged by measuring and evaluating the environmental assessment points of the atmospheric environment.

Additionally, according to the deterioration diagnosis method of the invention in the present Patent Application, with regard to electronic circuit parts made from the metallic material that composes the electronic circuit, a prescribed corrosion deterioration limiting value for the adjudged corrosion deterioration state is converted to a corrosion loss limiting value or a corrosion speed limiting value for the metallic material composing an electronic circuit part by applying it to the relationship between the corrosion loss or corrosion speed and the corrosion deterioration indices for an electronic circuit part that is made from the relevant metallic material.

Therefore, it is possible to judge the corrosion limit of that electronic circuit part by measuring and evaluating the atmospheric environmental assessment points and finding the corrosion loss or corrosion speed of the metallic material composing the electronic circuit part.

Additionally, according to the deterioration diagnosis method of the invention in the present patent application, when the metallic material composing the electronic circuit is copper and the electronic circuit part is the copper wiring pattern, the corrosion deterioration limiting value is taken as the limiting percentage corrosion thickness loss of the copper wiring pattern.

Therefore, the corrosion deterioration limit of that copper wiring pattern can be judged by measuring and evaluating the environmental assessment points of the atmospheric environment and finding the corrosion loss or corrosion speed of the copper wiring pattern.

Additionally, according to the deterioration diagnosis method of the invention in the present Patent Application, when the metallic material composing the electronic circuit is aluminium and the electronic circuit part is an integrated circuit, the corrosion deterioration limiting value is taken as the limiting corroded area percentage of the aluminium wiring of the integrated circuit.

Therefore, the corrosion deterioration limit of that integrated circuit aluminium wiring can be judged by measuring and evaluating the environmental assessment points of the atmospheric environment and finding the corrosion loss or corrosion speed of the aluminium wiring.

Additionally, according to the deterioration diagnosis method of the invention in the present Patent Application, when the metallic material composing the electronic circuit is silver and the electronic circuit part is a silver contact, the corrosion deterioration limiting value is taken as the limiting contact resistance value of the silver contact.

Therefore, the corrosion deterioration limit of that silver contact can be judged by measuring and evaluating the environmental assessment points of the atmospheric environment and finding the corrosion loss or corrosion speed of the silver contact.

Additionally, according to the deterioration diagnosis method of the invention in the present Patent Application, it has been designed to calculate environmental assessment points using the method of the invention in the present Patent Application.

Therefore, the harmfulness of an atmospheric environment toward metallic materials can be easily evaluated using environmental assessment points found by inverse calculation from the number of days' exposure and corrosion loss of a specific metallic material.

Additionally, according to the deterioration diagnosis method of the invention in the present Patent Application, a correlation function for the contamination level and the deterioration index of an electronic circuit substrate surface are found and stored in advance. The contamination level of the electronic circuit substrate in the electronic apparatus that is the diagnosis subject is measured, and this measured contamination level is converted to a deterioration index by applying the above correlation function. Then, the life span of the above electronic apparatus is diagnosed using this deterioration index.

Therefore, the life span of an electronic apparatus can be diagnosed by measuring the contamination level of an electronic circuit substrate surface.

Additionally, according to the deterioration diagnosis method of the invention in the present Patent Application, a correlation function for the contamination level and the deterioration index of an electronic circuit substrate surface are found and stored in advance. The existing contamination level of the electronic circuit substrate in the electronic apparatus that is the diagnosis subject and its contamination level after the elapse of a specified period are respectively measured, and the variation with passage of time of the deterioration index is found by applying each of these measured contamination levels respectively to the correlation function. Then, the life span of the electronic apparatus is diagnosed by this time-wise variation of the deterioration index.

Therefore, the life span of an electronic apparatus can be diagnosed by measuring the contamination levels of an electronic circuit substrate in the existing state and level after the elapse of a specified period, without the need for withdrawing the electronic circuit substrate and its destructive testing.

Additionally, according to the deterioration diagnosis method of the present invention, the correctional function of the environmental assessment points and the contamination level is calculated in advance. The amount of each of a plurality of environmental factors, including temperature, humidity, corrosive gas, sea salt particles under the atmospheric conditions or a distance from the coast, are determined by applying environmental assessment points, calculated from a sum of products of amounts of each factor and a weighting coefficient for each factor applied according to the amount of each factor, to the correctional function.

Therefore, by the measurement and evaluation of the environmental assessment points of the atmospheric conditions of the contamination level instead of the direct measurement, the life span of the electronic instrument can be diagnosed based on the contamination level converted from the environmental assessment points and without destruction, even in a case where the electronic circuit substrate is arranged at the rear side of the control panel, where the direct measurement of the contamination level is difficult, etc.

Additionally, according to the deterioration diagnosis method of the present invention, an adhered amount of anions, including chlorine ions, nitrate ions and sulfate ions, adhered on the surface of the electronic circuit board per unit area, is used as the contamination level.

Therefore the life span of the electronic instrument can be diagnosed by measuring the adhered amount of anions on the surface of the electronic circuit substrate with the most substantial influence on lowered insulation and corrosion.

Additionally, according to the deterioration diagnosis method of the present invention, the deterioration index is the variation rate of fractal dimension of the temperature distribution image of the electronic circuit substrate.

Therefore the rate of fractal dimension change can be calculated by a single measurement of the contamination level of the surface of the electronic circuit substrate without the measurement of the heat distribution of the electronic circuit substrate nor the fractal dimension change calculation, which requires a particular apparatus to operate the measurement, and the life span of the electronic instrument can be diagnosed.

Additionally, according to the deterioration diagnosis method of the present invention, the deterioration index is a wire breaking time of a conductor pattern of the electronic circuit substrate, and so the wire breaking time of a conductor pattern of the electronic circuit substrate can be calculated by measuring the contamination level of the surface of the electronic circuit substrate, and the life span of the electronic instrument can be diagnosed.

Additionally, according to the deterioration diagnosis method of the present invention, the deterioration index is the insulation resistance value between the conductors of the electronic circuit.

Therefore the insulation resistance value between the connector leads or the component leads, which is difficult to measure actually, can be calculated by measuring the contamination level of the surface of the electronic circuit substrate, and the life span of the electronic instrument can be diagnosed.

Additionally, according to the deterioration diagnosis apparatus of the present invention, contamination level calculation means (unit) for calculating the contamination level of the surface of the electronic circuit substrate and the contamination speed, a deterioration index database for storing the correlation function of the contamination level of the electronic circuit substrate and the deterioration index; deterioration index calculation means (unit) for calculating the deterioration index value corresponding to a measured contamination value, outputted from deterioration level measurement means (unit), and the correctional function read out from the deterioration index database; a life span database storing life span threshold values for the deterioration index of the electronic circuit board; contamination level difference calculation means (unit) for calculating a contamination level difference corresponding to a difference between a current deterioration index value and a life span threshold value read out from the life span database, from a correctional function read out from the deterioration index database; and remaining life span calculation means (unit) for calculating the remained life span by dividing the contamination level difference, calculated by the contamination level difference calculation means (unit), using contamination speed outputted from the contamination level measurement means are provided.

Therefore a series of the necessary processes such as calculation, etc. are carried out by measuring the contamination level of the surface of the electronic circuit substrate and the contamination speed, and the life span of the electronic instrument can be diagnosed with high accuracy.

Obviously, numerous additional modifications and variations of the present invention are possible in light of the above teachings, It is therefore to be understood that within the scope of the appended claims, the present invention may be practiced otherwise than as specially described herein.

What is claimed is:

1. A deterioration diagnosis method, comprising the steps of:

formulating a corrosion loss of a metallic material to exposure days under an atmospheric condition as a function of environmental assessment points which represent a level of harmfulness of said atmospheric condition; and diagnosing a life span of said metallic material based upon said corrosion loss calculated by using said function;

wherein said environmental assessment points are a sum of multiplications of separate assessment points for each of a plurality of environmental factors, including temperature, humidity, corrosive gas, and a distance from a coast, assigned to each factor according to an amount of each factor, and a weighting coefficient for each factor.

2. A deterioration diagnosis method, comprising the steps of:

formulating a corrosion speed of a metallic material under an atmospheric condition as a function of environmental assessment points which represent a level of harmfulness of said atmospheric condition; and diagnosing a life span of said metallic material based upon said corrosion speed calculated by using said function;

wherein said environmental assessment points are a sum of multiplications of separate assessment points for each of a plurality of environmental factors, including temperature, humidity, corrosive gas, and a distance from a coast, assigned to each factor according to an amount of each factor, and a weighting coefficient for each factor.

3. The deterioration diagnosis method according to claim 2, wherein for an atmospheric environment where said metallic material is used, a plurality of environmental factors, including temperature, humidity, corrosive gas, sea salt particles in said atmospheric environment or a distance from a coast, are measured for a prescribed period;

said assessment points for each factor are determined by being classified according to a range of said amount of each environmental factor, or are a function of median of said amount of each environmental factor; and a corrosion speed of said metallic material is determined using said determined environmental assessment points.

4. A computer readable medium configured to instruct a computer to carry out said method disclosed in claim 1 or 2.

5. A deterioration diagnosis method comprising the steps of:

formulating a corrosion loss of a metallic material to exposure days under an atmospheric condition as a function of environmental assessment points which represent a level of harmfulness of said atmospheric condition; and diagnosing a life span of said metallic material based upon said corrosion loss calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein assessment points for each of said plurality of environmental factor including temperature, humidity, corrosive gas, sea salt particles in said atmospheric environment, or said distance from said coast are applied after being classified according to a range of said amount of each environmental factor, or are a function of median of said amount of each environmental factor.

6. A deterioration diagnosis method comprising the steps of:

formulating a corrosion lass of a metallic material to exposure days under an atmospheric condition as a function of environmental assessment points which represent a level of harmfulness of said atmospheric condition; and diagnosing a life span of said metallic material based upon said corrosion loss calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein said method is a filter paper method, in which an amount of gas absorbed on a filter exposed for a prescribed period is calculated as an amount of the corrosive gas, is utilized for a measurement method for an amount of corrosive gas as an environmental factor;

an amount of acid gas included in said corrosive gas is measured with an alkaline filter paper, which is made of cellulose and impregnated with either of a potassium carbonate solution of a prescribed % or a sodium carbonate solution of a prescribed %; and an amount of alkaline gas included in said corrosive gas is measured with an acid filter paper, which is made of glass and impregnated a phosphoric acid solution of a prescribed %.

7. A deterioration diagnosis method comprising the steps of:

formulating a corrosion loss of a metallic material to exposure days under an atmospheric condition as a function of environmental assessment points which represent a level of harmfulness of said atmospheric condition; and diagnosing a life span of said metallic material based upon said corrosion loss calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein a specified metallic material is exposed under said atmospheric environment for prescribed period;

an amount of weight loss due to corrosion is measured during exposure days of a prescribed period;

said environmental assessment points are calculated by the amount of the weight loss due to corrosion and the exposure days; and a life span of another metallic material under said atmospheric condition is diagnosed by using said calculated environmental assessment points.

8. The deterioration diagnosis method according to claim 7, wherein a copper is used for said specified metallic material.

9. A deterioration diagnosis method comprising the steps of:

formulating a corrosion loss of a metallic material to exposure days under an atmospheric condition as a function of environmental assessment points which represent a level of harmfulness of said atmospheric condition; and diagnosing a life span of said metallic material based upon said corrosion loss calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein an amount of weight loss due to corrosion of said metallic material in an atmospheric environment is represented by a linear expression of a square root of number of exposure days of said metallic material in said atmospheric environment, and coefficients in said linear expression are represented by a multinomial expression of said environmental assessment points.

10. A deterioration diagnosis method comprising the steps of:

formulating a corrosion loss of a metallic material to exposure days under an atmospheric condition as a function of environmental assessment points which represent a level of harmfulness of said atmospheric condition; and diagnosing a life span of said metallic material based upon said corrosion loss calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein corrosion speed is represented by a linear expression of a square root of the number of exposure days of said metallic material in an atmospheric environment, and coefficients in said linear expression are represented by a multinomial expression of said environmental assessment points.

11. A deterioration diagnosis method comprising the steps of:

formulating a corrosion loss of a metallic material to exposure days under an atmospheric condition as a function of environmental assessment points which represent a level of harmfulness of said atmospheric condition; and diagnosing a life span of said metallic material based upon said corrosion loss calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein for an atmospheric environment where said metallic material is used, a plurality of environmental factors, including temperature, humidity, corrosive gas, sea salt particles in said atmospheric conditions or a distance from a coast, are measured for a prescribed period;

said assessment points for each factor are determined as a function of median of said amount of each environmental factor using each of measured values;

said environmental assessment points are determined by using said determined assessment points for each factor;

a relationship between said corrosion loss of a metallic material and said number of exposure days is determined using said determined environmental assessment points.

12. A deterioration diagnosis method comprising the steps of:

formulating a corrosion speed of a metallic material under an atmospheric condition as a function of environmental assessment points which represent a level of harmfulness of said atmospheric condition; and diagnosing a life span of said metallic material based upon said corrosion speed calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein for an atmospheric environment where said metallic material is used, said environmental assessment points are calculated by the amount of weight loss due to corrosion and the exposure days;

a relationship between said corrosion loss of said metallic material and said number of exposure days is determined using said determined environmental assessment points.

13. The deterioration diagnosis method according to claim 11 or claim 12, wherein a metallic material is exposed under an atmospheric environment for a prescribed period;

corrosion loss of said metallic material for a number of exposure days in a prescribed period is measured; and a relationship between an amount of said corrosion loss and said number of exposure days calculated by said method disclosed in claim 13 or 14 is corrected using said measurement results.

14. The deterioration diagnosis method according to claim 13, wherein for a metallic material constituting an electronic circuit, said calculated corrosion loss or said compensated corrosion loss is converted to a corrosion deterioration index for an electronic circuit component by applying a relationship between said corrosion loss prepared in advance for said metallic material constituting an electronic circuit and said corrosion deterioration index of said electronic circuit component formed of said metallic material; and a corrosion deterioration condition of an electronic circuit component is judged according to said corrosion deterioration index.

15. The deterioration diagnosis method according to claim 14, wherein a copper is used for said metallic material for said electronic circuit;

a copper wiring pattern is used for an electronic circuit component; and said corrosion deterioration index is a thickness of corrosion of said copper wiring pattern.

16. The deterioration diagnosis method according to claim 14, wherein an aluminum is used for said metallic material for said electronic circuit;

an integrated circuit is used for said electronic circuit component; and said corrosion deterioration index is a corroded area rate of aluminum wiring of said integrated circuit.

17. The deterioration diagnosis method according to claim 14, wherein a silver is used for said metallic material for said electronic circuit;

a silver contact point is used for an electronic circuit component; and said corrosion deterioration index is a contact resistance value of said silver contact point.

18. The deterioration diagnosis method according to claim 14, wherein a judged corrosion deterioration limit value set for a corrosion deterioration condition is converted to a limit value of corrosion weight loss of said metallic material composing said electronic circuit component, by applying said relationship between said corrosion loss and said corrosion deterioration index of said electronic circuit component composed of said metallic material.

19. The deterioration diagnosis method according to claim 18, wherein a copper is used for said metallic material constituting electronic circuit;

a copper wiring pattern is used for said electronic circuit component; and said corrosion deterioration limit is a rate of decreased thickness limit due to corrosion of said copper wiring pattern.

20. The deterioration diagnosis method according to claim 18, wherein an aluminum is used for said metallic material for said electronic circuit;

an integrated circuit is used for said electronic circuit component; and said corrosion deterioration limit is a rate of corroded area of aluminum wiring of said integrated circuit.

21. The deterioration diagnosis method according to claim 18, wherein a silver is used for said metallic material for said electronic circuit;

a silver contact point is used for said electronic circuit component;

and said corrosion deterioration limit is a contact resistance limit value of said silver contact point.

22. A deterioration diagnosis method comprising the steps of:
- formulating a corrosion speed of a metallic material under an atmospheric condition as a function of environmental assessment points which represent a level of harmfulness of said atmospheric condition; and
- diagnosing a life span of said metallic material based upon said corrosion speed calculated by using said function;
- wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;
- wherein for an atmospheric environment where said metallic material is used, said environmental assessment points are calculated by the amount of the weight loss due to corrosion and the exposure days; and
- a corrosion speed of said metallic material is determined according to said calculated environmental assessment points.

23. The deterioration diagnosis method according to claim 3 or claim 22,
- wherein said metallic material is exposed under an atmospheric environment for a prescribed period;
- corrosion loss of said metallic material for a number of exposure days in a prescribed period is measured; and
- corrosion speed of said metallic material calculated is corrected using said measurement results.

24. A deterioration diagnosis equipment, comprising:
- an input unit for inputting a measured value of an amount of each environmental factor measured by an environmental factor amount measurement unit, wherein said environmental factors include a distance from a coast;
- a first database for storing a function giving a relationship to an amount of each environmental factor and assessment points for each factor,
- a second database for storing function giving relationships between environmental assessment points and assessment points for each factor for each type of metallic material,
- a plurality of assessment points for each factor calculation unit for calculating said assessment points far each factor using said function read out from said first database and an amount of each environmental factor input by said input unit;
- an environmental assessment points calculation unit for calculating environmental assessment points which represent a level of the harmfulness of an atmospheric environment using said function read out from said second database and each environment factor calculated by said assessment points for each factor calculation;
- a corrosion loss calculation unit for calculating a relationship between an amount of corrosion loss of said metallic material under said atmospheric environment and a number of exposure days using a function in which environmental assessment points calculated by said environmental assessment points calculation unit are formulated as a variable;
- a corrosion speed calculation unit for calculating said corrosion speed of a metallic material under said atmospheric environment using a function in which said environmental assessment points calculated by said environmental assessment points calculation unit are formulated as a variable;
- a corrosion loss correction calculation unit for correcting said relationship between said corrosion loss and said number of exposure days calculated by said corrosion loss calculation unit based on said corrosion loss of said metallic material in said number of exposure days of said prescribed period;
- a corrosion speed calculation unit for correcting said corrosion speed calculated by said corrosion speed calculation mean based on said amount of corrosion loss of said metallic material in said number of exposure days of said prescribed period;
- a remaining life span calculation unit for calculating a remaining life span of said metallic material based on said relationship between said corrosion loss corrected by said corrosion loss correction unit and said number of exposure days, or based on said corrosion speed corrected by said corrosion speed correction unit; and
- an output unit for outputting said remaining life span of each metallic material calculated by said remaining life span calculation unit as diagnosis result.

25. A deterioration diagnosis method comprising the steps of:
- formulating a corrosion loss of a metallic material to exposure days under an atmospheric condition as a function of environmental assessment points which represent a level of harmfulness of said atmospheric condition;
- diagnosing a life span of said metallic material based upon said corrosion loss calculated by using said function; and
- evaluating harmfulness of an atmospheric environment on a metallic material by performing an atmospheric environment classification method using environmental assessment points, wherein said environmental assessment points are calculated by the amount of weight loss due to corrosion and the exposure days;
- wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor.

26. A deterioration diagnosis method comprising the steps of:
- formulating a corrosion loss of a metallic material to exposure days under an atmospheric condition as a function of environmental assessment points which represent a level of harmfulness of said atmospheric condition; and
- diagnosing a life span of said metallic material based upon said corrosion loss calculated by using said function;
- wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein a correlation function of contamination level of a surface of an electronic circuit substrate and a deterioration index are calculated in advance;

said contamination level of said electronic circuit substrate of an electronic instrument as a subject of diagnosis target is measured;

said measured contamination level is converted to said deterioration index by applying said measured contamination level in a correctional function; and said remaining life span of said electronic instrument is diagnosed according to said deterioration index.

27. The deterioration diagnosis method according to claim 26, wherein said correctional function of said environmental assessment points and said contamination level is calculated in advance;

an amount of each of a plurality of environmental factors, including temperature, humidity, corrosive gas, sea salt particles under an atmospheric environment or a distance from the coast, are determined by applying environmental assessment points, calculated from a sum of multiplications of amounts of each factor and a weighting coefficient for each factor applied according to said amount of each factor, to said correctional function.

28. The deterioration diagnosis method according to claim 26, wherein a adhered amount of anions, including chlorine ions, nitrate ions and sulfate ions, adhered on a surface of an electronic circuit board per unit area is used as said contamination level.

29. The deterioration diagnosis method according to claim 26, wherein said deterioration index is a vibration rate of fractal dimension of a temperature distribution image of an electronic circuit substrate.

30. The deterioration diagnosis method according to claim 26, wherein said deterioration index is a wire breaking time of a conductor pattern of an electronic circuit substrate.

31. The deterioration diagnosis method according to claim 26, wherein said deterioration index is an insulation resistance value between conductors of an electronic circuit board.

32. A deterioration diagnosis method comprising the steps of:

formulating a corrosion loss of a metallic material to exposure days under an atmospheric condition as a function of environmental assessment points which represent a level of harmfulness of said atmospheric condition; and diagnosing a life span of said metallic material based upon said corrosion loss calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein a correlation function between a contamination level of a surface of an electronic circuit substrate and a deterioration corrosion is calculated in advance;

said current contamination level of said electronic circuit substrate of an electronic instrument as a diagnosis target and a contamination level after a prescribed period are respectively measured;

a change with time of deterioration index is calculated by applying each measured contamination level to said correctional function; and said remaining life span of the electronic instrument is diagnosed according to said change with time of said deterioration index.

33. A deterioration diagnosis method comprising the steps of:

formulating a corrosion speed of a metallic material under an atmospheric condition as a function of environmental assessment points which represent a level of harmfulness of said atmospheric condition; and diagnosing a life span of said metallic material based upon said corrosion speed calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein for an atmospheric environment where said metallic material is used, the plurality of environmental factors, including temperature, humidity, corrosive gas, sea salt particles in said atmospheric environment or the distance from a coast, are measured for a prescribed period;

said assessment points for each factor are determined by being classified according to a range of said amount of each environmental factor, or are a function of median of said amount of each environmental factor; and a corrosion speed of said metallic material is determined using said determined environmental assessment points;

wherein said metallic material is exposed under an atmospheric environment for a prescribed period;

corrosion loss of said metallic material for a number of exposure days in a prescribed period is measured; and corrosion speed of said metallic material calculated is corrected using said measurement results;

wherein for a metallic material constituting an electronic circuit, said calculated corrosion speed or said compensated corrosion speed is converted to a corrosion deterioration index for an electronic circuit component by applying a relationship between said corrosion speed prepared in advance for said metallic material constituting an electronic circuit or said corrosion speed and said corrosion deterioration index of said electronic circuit component formed of said metallic material; and a corrosion deterioration condition of an electronic circuit component is judged according to said corrosion deterioration index.

34. The deterioration diagnosis method according to claim 33, wherein a copper is used for said metallic material for said electronic circuit;

a copper wiring pattern is used for an electronic circuit component; and said corrosion deterioration index is a thickness of corrosion of said copper wiring pattern.

35. The deterioration diagnosis method according to claim 33,
wherein an aluminum is used for said metallic material for said electronic circuit;
an integrated circuit is used for said electronic circuit component; and
said corrosion deterioration index is a corroded area rate of aluminum wiring of said integrated circuit.

36. The deterioration diagnosis method according to claim 33,
wherein a silver is used for said metallic material for said electronic circuit;
a silver contact point is used for an electronic circuit component; and
said corrosion deterioration index is a contact resistance value of said silver contact point.

37. The deterioration diagnosis method according to claim 33,
wherein a judged corrosion deterioration limit value set for a corrosion deterioration condition is converted to a limit value of corrosion speed of said metallic material composing said electronic circuit component, by applying said relationship between said corrosion speed and said corrosion deterioration index of said electronic circuit component composed of said metallic material.

38. The deterioration diagnosis method according to claim 37,
wherein a copper is used for said metallic material constituting electronic circuit;
a copper wiring pattern is used for said electronic circuit component; and
said corrosion deterioration limit is a rate of decreased thickness limit due to corrosion of said copper wiring pattern.

39. The deterioration diagnosis method according to claim 37,
wherein an aluminum is used for said metallic material for said electronic circuit;
an integrated circuit is used for said electronic circuit component; and
said corrosion deterioration limit is a rate of corroded area of aluminum wiring of said integrated circuit.

40. The deterioration diagnosis method according to claim 37,
wherein a silver is used for said metallic material for said electronic circuit;
a silver contact point is used for said electronic circuit component;
and said corrosion deterioration limit is a contact resistance limit value of said silver contact point.

41. A deterioration diagnosis method comprising the steps of:
formulating a corrosion speed of a metallic material under an atmospheric condition as a function of environmental assessment points which represent a level of harmfulness of said atmospheric condition; and
diagnosing a life span of said metallic material based upon said corrosion speed calculated by using said function;
wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor.

42. The deterioration diagnosis method according to claim 5 or claim 41,
wherein said assessment points for each factor due to a range of mount of each environmental factor are divided into at least 5 classes.

43. The deterioration diagnosis method according to claim 42,
wherein said assessment points for a mutual humidity in atmospheric environment where an object is exposed directly to rain and snow are calculated as a sum of said assessment points in each class and the prescribed correctional points.

44. The deterioration diagnosis method according to claim 42,
wherein assessment points for sea salt particles as an environmental factor are applied due to a classification by a distance from said coast.

45. A deterioration diagnosis method, comprising the steps of:
formulating a corrosion speed of a metallic material under an atmospheric condition as a function of environmental assessment points which represent a level of harmfulness of said atmospheric condition; and
diagnosing a life span of said metallic material based upon said corrosion speed calculated by using said function;
wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;
wherein said method is a filter paper method, in which an amount of gas absorbed on a filter exposed for a prescribed period is calculated as an amount of the corrosive gas, is utilized for a measurement method for an amount of corrosive gas as an environmental factor;
an amount of acid gas included in said corrosive gas is measured with an alkaline filter paper, which is made of cellulose and impregnated with either of a potassium carbonate solution of a prescribed % or a sodium carbonate solution of a prescribed %; and
an amount of alkaline gas included in said corrosive gas is measured with an acid filter paper, which is made of glass and impregnated with a phosphoric acid solution of a prescribed %.

46. A deterioration diagnosis method, comprising the steps of:
formulating a corrosion speed of a metallic material under an atmospheric condition as a function of environmental assessment points which represent a level of harmfulness of said atmospheric condition; and
diagnosing a life span of said metallic material based upon said corrosion speed calculated by using said function;
wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein an amount of weight loss due to corrosion of said metallic material in an atmospheric environment is represented by a linear expression of a square root of number of exposure days of said metallic material in said atmospheric environment, and coefficients in said linear expression are represented by a multinomial expression of said environmental assessment points.

47. A deterioration diagnosis method, comprising the steps of:

formulating a corrosion speed of a metallic material under an atmospheric condition as a function of environmental assessment points which represent a level of harmfulness of said atmospheric condition; and diagnosing a life span of said metallic material based upon said corrosion speed calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein corrosion speed is represented by a linear expression of a square root of the number of exposure days of said metallic material in an atmospheric environment, and coefficients in said linear expression are represented by a multinomial expression of said environmental assessment points.

48. A deterioration diagnosis method, comprising the steps of:

formulating a corrosion speed of a metallic material under an atmospheric condition as a function of environmental assessment points which represent a level of harmfulness of said atmospheric condition; and diagnosing a life span of said metallic material based upon said corrosion speed calculated by using said function; and evaluating harmfulness of an atmospheric environment on a metallic material by performing an atmospheric environment classification methods using environmental assessment points, wherein said environmental assessment points are calculated by the amount of weight loss due to corrosion and the exposure days;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor.

49. A deterioration diagnosis method, comprising the steps of:

formulating a corrosion speed of a metallic material under an atmospheric condition as a function of environmental assessment points which represent a level of harmfulness of said atmospheric condition; and diagnosing a life span of said metallic material based upon said corrosion speed calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein a correlation function of contamination level of a surface of an electronic circuit substrate and a deterioration index are calculated in advance;

said contamination level of said electronic circuit substrate of an electronic instrument as a subject of diagnosis target is measured;

said measured contamination level is converted to said deterioration index by applying said measured contamination level in a correctional function; and said remaining life span of said electronic instrument is diagnosed according to said deterioration index.

50. A deterioration diagnosis method, comprising the steps of:

formulating a corrosion speed of a metallic material under an atmospheric condition as a function of environmental assessment points which represent a level of harmfulness of said atmospheric condition; and diagnosing a life span of said metallic material based upon said corrosion speed calculated by using said function;

wherein said environmental assessment points are a sum of multiplications of separate assessment points for each of a plurality of environmental factors, including temperature, humidity, corrosive gas, sea salt particles in an atmospheric environment, or a distance from a coast, assigned to each factor according to an amount of each factor, and a weighting coefficient for each factor;

wherein a correlation function between a contamination level of a surface of an electronic circuit substrate and a deterioration corrosion is calculated in advance;

said current contamination level of said electronic circuit substrate of an electronic instrument as a diagnosis target and a contamination level after a prescribed period are respectively measured;

a change with time of deterioration index is calculated by applying each measured contamination level to said correctional function; and said remaining life span of the electronic instrument is diagnosed according to said change with time of said deterioration index.

* * * * *